US012704901B2

(12) United States Patent
Faeulhammer et al.

(10) Patent No.: US 12,704,901 B2
(45) **Date of Patent: *Aug. 11, 2026**

(54) BENDING-ASSISTED CALIBRATION FOR EXTENDED REALITY TRACKING

(71) Applicant: Snap Inc., Santa Monica, CA (US)

(72) Inventors: Thomas Faeulhammer, Vienna (AT); Matthias Kalkgruber, Vienna (AT); Thomas Muttenthaler, Vienna (AT); Tiago Miguel Pereira Torres, Vienna (AT); Daniel Wolf, Mödling (AT)

(73) Assignee: Snap Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/058,864

(22) Filed: Feb. 20, 2025

(65) Prior Publication Data

US 2025/0190050 A1 Jun. 12, 2025

Related U.S. Application Data

(63) Continuation of application No. 18/478,352, filed on Sep. 29, 2023, now Pat. No. 12,271,517.

(51) Int. Cl.
*G06F 3/01* (2006.01)
*A61B 5/16* (2006.01)
*G06T 17/00* (2006.01)

(52) U.S. Cl.
CPC ................ *G06F 3/012* (2013.01); *A61B 5/16* (2013.01); *G06T 17/00* (2013.01)

(58) Field of Classification Search
CPC .... G06F 3/011–012; A61B 5/16; G06T 17/00
See application file for complete search history.

(56) References Cited

U.S. PATENT DOCUMENTS 12,271,517 B1 4/2025 Faeulhammer et al.
12,475,202 B2 11/2025 Katz
(Continued)

FOREIGN PATENT DOCUMENTS

KR 20200011818 2/2020
WO 2025072727 4/2025

OTHER PUBLICATIONS

"Korean Application Serial No. 10-2023-7043024, Notice of Preliminary Rejection mailed Feb. 11, 2025", w English translation, 15 pgs.

(Continued)

*Primary Examiner* — Hang Lin
(74) *Attorney, Agent, or Firm* — Schwegman Lundberg & Woessner, P.A.

(57) ABSTRACT

Bending data is used to facilitate tracking operations of an extended reality (XR) device, such as hand tracking or other object tracking operations. The XR device obtains bending data indicative of bending of the XR device to accommodate a body part of a user wearing the XR device. The XR device determines, based on the bending data, whether to use previously identified biometric data in a tracking operation. A mode of the XR device is selected based on this determination. The XR device performs the tracking operation based on the selected mode. The selected mode may be a first mode in which the previously identified biometric data is used in the tracking operation or a second mode which does not apply previously identified biometric data in the tracking operation.

20 Claims, 13 Drawing Sheets

(56) References Cited

U.S. PATENT DOCUMENTS

| | | | | |
|---|---|---|---|---|
| 2019/0018396 | A1 | 1/2019 | Gorsuch et al. | |
| 2022/0334649 | A1 * | 10/2022 | Hwang | G06F 3/04817 |
| 2022/0374505 | A1 * | 11/2022 | Katz | G06V 20/20 |
| 2025/0110547 | A1 | 4/2025 | Faeulhammer et al. | |
| 2026/0050660 | A1 | 2/2026 | Katz | |

OTHER PUBLICATIONS

"U.S. Appl. No. 18/478,352, PTO Response to Rule 312 Communication mailed Mar. 14, 2025", 2 pgs.
"U.S. Appl. No. 17/489,394, Response filed Apr. 25, 2025 to Non Final Office Action mailed Feb. 7, 2025", 13 pgs.
"U.S. Appl. No. 18/478,352, 312 Amendment filed Feb. 18, 2025", 3 pgs.
"U.S. Appl. No. 18/478,352, Notice of Allowance mailed Nov. 22, 2024", 10 pgs.
"U.S. Appl. No. 18/478,352, Supplemental Notice of Allowability mailed Jan. 22, 2025", 2 pgs.
"U.S. Appl. No. 18/478,352, Supplemental Notice of Allowability mailed Dec. 11, 2024", 2 pgs.
"U.S. Appl. No. 17/489,394, Notice of Allowance mailed Jul. 21, 2025", 20 pgs.
"European Application Serial No. 22735273.9, Communication Pursuant to Article 94(3) EPC mailed Dec. 23, 2025", 7 pgs.
"Korean Application Serial No. 10-2023-7043024, Notice of Preliminary Rejection mailed Oct. 27, 2025", w/ English Translation, 7 pgs.
"European Application Serial No. 22735273.9, Response to Communication pursuant to Rules 161(2) and 162 EPC filed Jul. 3, 2024", 17 pgs.
"Korean Application Serial No. 10-2023-7043024, Response Filed Apr. 8, 2025 to Notice of Preliminary Rejection mailed Feb. 11, 2025", w/ English Claims and translation, 32 pgs.

* cited by examiner

BENDING-ASSISTED CALIBRATION FOR EXTENDED REALITY TRACKING

CLAIM OF PRIORITY

This application is a continuation of U.S. patent application Ser. No. 18/478,352, filed on Sep. 29, 2023, which is incorporated herein by reference in its entirety.

TECHNICAL FIELD

The subject matter disclosed herein generally relates to extended reality (XR). More specifically, but not exclusively, the subject matter relates to the use of bending data to facilitate tracking operations, such as hand tracking operations, performed by an XR device.

BACKGROUND

Object tracking is an important function of many XR devices. Objects in the real world can be tracked to provide realistic, entertaining, or useful XR experiences, e.g., by displaying virtual content based on the position or movements of a tracked object. For example, some XR devices use hand gestures as an input. This enables a user to interact with an XR device without a traditional input device, such as a touchpad or controller, but requires swift and accurate hand tracking.

BRIEF DESCRIPTION OF THE SEVERAL VIEWS OF THE DRAWINGS

In the drawings, which are not necessarily drawn to scale, like numerals may describe similar components in different views. To identify the discussion of any particular element or act more easily, the most significant digit or digits in a reference number refer to the figure number in which that element is first introduced. Some non-limiting examples are illustrated in the figures of the accompanying drawings in which.

DETAILED DESCRIPTION

Figure 1:
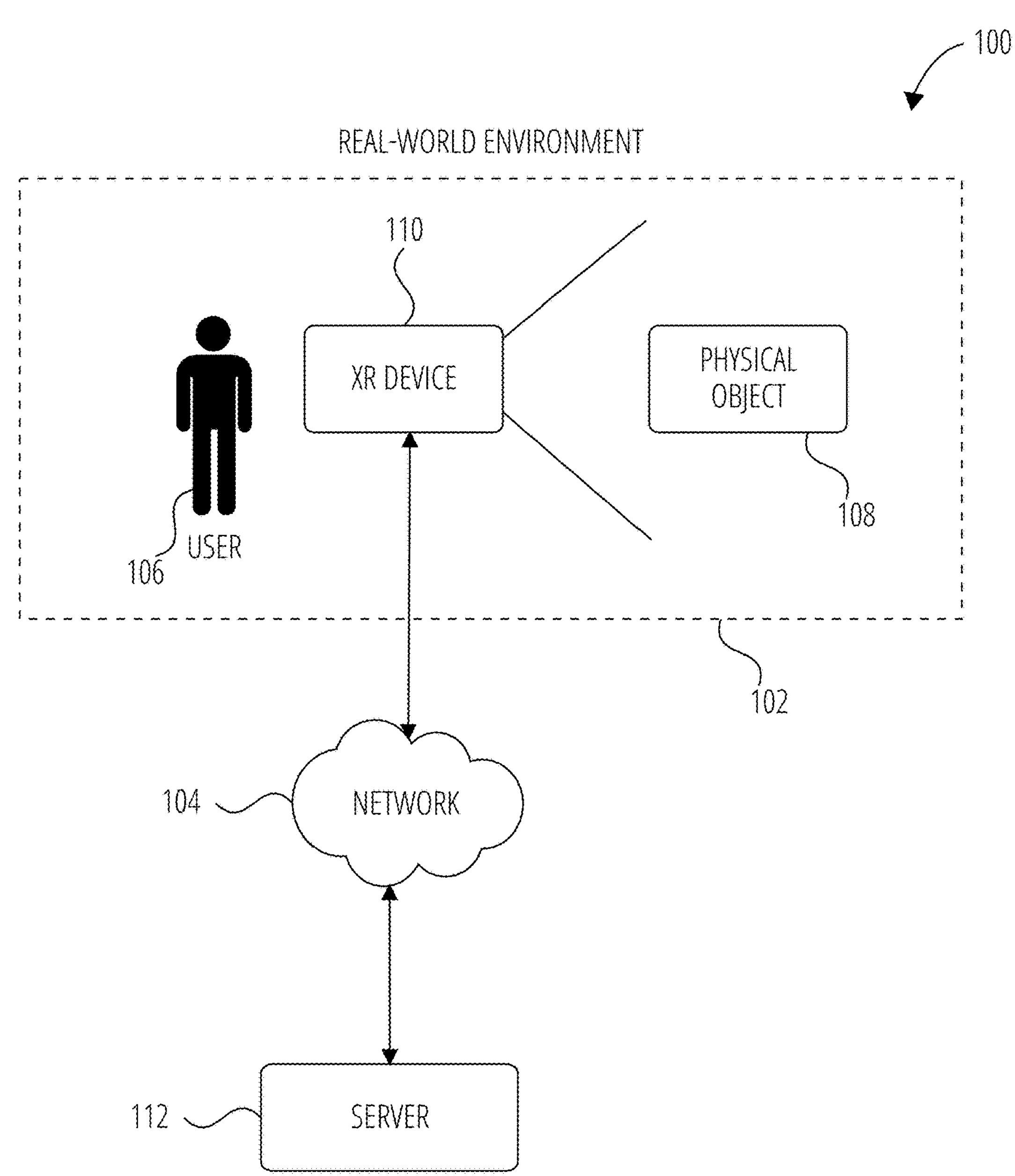
FIG. 1 is a block diagram illustrating a network environment for operating an XR device, according to some examples.

The description that follows describes systems, methods, devices, techniques, instruction sequences, or computing machine program products that illustrate examples of the present subject matter. In the following description, for purposes of explanation, numerous specific details are set forth in order to provide an understanding of various examples of the present subject matter. It will be evident, however, to those skilled in the art, that examples of the present subject matter may be practiced without some or other of these specific details. Examples merely typify possible variations. Unless explicitly stated otherwise, structures (e.g., structural components) are optional and may be combined or subdivided, and operations (e.g., in a procedure, algorithm, or other function) may vary in sequence or be combined or subdivided.

The term "augmented reality" (AR) is used herein to refer to an interactive experience of a real-world environment where physical objects or environments that reside in the real world are "augmented" or enhanced by computer-generated digital content (also referred to as virtual content or synthetic content). An AR device can enable a user to observe a real-world scene while simultaneously seeing virtual content that may be aligned to objects, images, or environments in the field of view of the AR device. AR can also refer to a system that enables a combination of real and virtual worlds, real-time interaction, and three-dimensional (3D) registration of virtual and real objects. A user of an AR system can perceive virtual content that appears to be attached or interact with a real-world physical object. The term "AR application" is used herein to refer to a computer-operated application that enables an AR experience.

The term "virtual reality" (VR) is used herein to refer to a simulation experience of a virtual world environment that is distinct from the real-world environment. Computer-generated digital content is displayed in the virtual world environment. A VR device can thus provide a more immersive experience than an AR device. The VR device may block out the field of view of the user with virtual content that is displayed based on a position and orientation of the VR device. VR also refers to a system that enables a user of a VR system to be completely immersed in the virtual world environment and to interact with virtual objects presented in the virtual world environment.

In general, AR and VR devices are referred to as "extended reality" (XR) devices, and related systems are referred to as XR systems. While examples described in the present disclosure focus primarily on XR devices that provide an AR experience, it will be appreciated that at least some aspects of the present disclosure may also be applied to other types of XR experiences.

The term "user session" is used herein to refer to an operation of an XR device, or an application of the XR device, by a user during a period of time. For example, a user session may refer to an operation of an AR application executing on a head-wearable XR device between the time the user puts on the XR device and the time the user takes off the head-wearable device. In some examples, the user session starts when the XR device is turned on or is woken up from sleep mode and stops when the XR device is turned off or placed in sleep mode. In other examples, the session starts when the user runs or starts an AR application, or runs or starts a particular feature of the AR application, and stops when the user ends the AR application or stops the particular features of the AR application.

The term "SLAM" (Simultaneous Localization and Mapping) is used herein to refer to a system used to understand and map a physical environment in real-time. It uses sensors such as cameras, depth sensors, and Inertial Measurement Units (IMUs) to capture data about the environment and then uses that data to create a map of the surroundings of a device while simultaneously determining the device's location within that map. This allows, for example, an XR device to accurately place digital objects in the real world and track their position as a user moves and/or as objects move.

The term "VIO" (Visual-Inertial Odometry) is used herein to refer to a technique that combines data from an IMU and a camera to estimate the pose of an object in real time. The term "pose" refers to the position and orientation of the object, e.g., the 3D position or translation (x, y, z) and orientation (yaw, pitch, roll), relative to a reference frame. A VIO system typically uses computer vision algorithms to analyze camera images and estimate the movement and position of the XR device, while also using IMU data to improve the accuracy and reliability of the estimates. By combining visual and inertial data, VIO may provide more robust and accurate tracking than using either sensor modality alone. In some examples, a VIO system may form part of a SLAM system, e.g., to perform the "Localization" function of the SLAM system.

The term "flexible device" is used herein to refer to an XR device (or a device forming part thereof) that is capable of bending, at least to some extent, without breaking. The term "bending" is used in a broad sense in the present disclosure to refer to any bending, deformation, or other mechanical or spatial change that may occur in an XR device to accommodate a body part (or body parts) of a user wearing the XR device. For example, in the case of a head-wearable XR device, the XR device may bend to accommodate the shape, features, or contours of the head of the user. The flexible device may, for example, be XR glasses that can bend without breaking to fit the head of the user. However, the term "flexible device" is not limited to head-wearable devices and may include other wearable XR devices.

The quick and accurate tracking of a user's hand is often required to provide an XR experience. However, hand tracking can present technical challenges. When observing the 3D real world via a two-dimensional (2D) image captured by a camera of an XR device, it may be challenging to predict or measure a distance between the hand and the camera with a high degree of accuracy. For example, a relatively large hand that is 50 cm away from the camera may appear to be (or be confused with) a smaller hand that is closer to the camera (e.g., 40 cm from the camera).

It is desirable to obtain an accurate estimate or measurement of one or more features of the hand, such as the size of the hand or relative positions of certain landmarks on the hand. This estimate or measurement can be applied to track the hand more accurately and provide a better XR experience, e.g., by accurately placing virtual content on or in relation to the hand.

To obtain such measurements or estimates of the hand, the XR device may perform a calibration operation (e.g., a dedicated hand feature calibration operation). The output of the calibration operation may be a calibration of one or more features of the hand (or hands), referred to in this disclosure as a "hand feature calibration." The hand feature calibration can be used to calibrate an object tracking system of the XR device and may include a set of parameters that describe the relevant hand features and the impact or relation to one or more tracking algorithms.

Given that a hand feature calibration is user-specific, it will not be useful (or will be significantly less useful) when another user uses the same XR device, particularly where the features of the hand of the other user differ substantially from the hand of the first user. For the same XR device to be used by multiple users, the XR device may recalibrate for every user session, e.g., in the case of a head-wearable XR device, each time the XR device is taken off and subsequently put on.

Alternatively, an XR device may store calibration data in association with a specific user's profile. In that way, when the user is logged into their user profile, the XR device is able to retrieve the calibration data. Both the former and latter options may create technical hurdles. The recalibration approach consumes processing resources and may reduce the accuracy or speed of a tracking operation. The user profile approach may result in data privacy or security issues, e.g., the XR device may either be configured not to store biometric data in association with a user's identity or it may be undesirable to do so. The latter approach also explicitly requires the user to provide their identity and have their identity linked to biometric features.

Examples of the present disclosure may address or alleviate the challenges described above by calibrating biometric features, e.g., calibrating for a user's hand size over one or more user session, while using XR device bending to determine which user corresponds to a particular user session.

Examples of the present disclosure provide a solution that does not require the "user profile approach." In other words, examples described herein provide a solution that does not require storing of biometric data in association with a user's identity.

In examples described herein, the need to store certain biometric data (e.g., a hand size) in association with an identifiable user profile is obviated by associating the biometric data with XR device bending measured across one or more user sessions. For example, the XR device may retain and/or refine a computed hand size for as long as no user switch is detected by the XR device. Where the XR device is a flexible device, a user switch may be detected by monitoring the bending of the flexible device.

The bending of an XR device to accommodate the body part of the user wearing the XR device may be measured or estimated using different devices or techniques. Over the years, more ergonomic and visually appealing frame designs for certain XR devices, such as AR glasses, have led to XR devices being more lightweight, but also less rigid. Flexible devices can thus be monitored to assess changes in spatial relations between different components, e.g., by comparing certain angles, dimensions, or forces in a wearing state to corresponding angles, dimensions, or forces in a non-wearing state. In some examples, bending can be measured by a strain gauge. In other examples, bending can be estimated using computer vision algorithms, e.g., by analyzing image data from cameras of the XR device that cover overlapping fields of view to determine a difference between a baseline overlap defined during manufacture and a modified overlap caused by bending during operation.

In some examples, a method includes obtaining bending data indicative of bending of an XR device to accommodate a body part of a user wearing the XR device. As mentioned, the XR device may be a flexible device and may be configured to determine, based on the bending data, whether to use previously identified biometric data in a tracking operation, e.g., a hand tracking operation or the tracking of another feature (e.g., another body part) of the user. Responsive to determining whether to use the previously identified biometric data, a mode of the XR device may be selected or adjusted.

The mode may be a first mode in which the previously identified biometric data is used in the tracking operation or a second mode in which the previously identified biometric data is not used in the tracking operation. The selected mode or adjusted mode may be used to initialize the tracking operation.

The previously identified biometric data may include a previously obtained or previously identified hand feature calibration. For example, the previously identified biometric data may be a hand size calibration or a calibration relating to another feature of a hand, such as measurements of a palm or other landmarks. The previously identified biometric data may include a hand feature estimate generated during a previous user session.

The bending data obtained by the XR device may include a measurement of the bending of the XR device generated by at least one sensor of the XR device (e.g., a strain gauge) and/or an estimate of the bending of the XR device (e.g., an estimate of bending obtained using a computer vision algorithm).

The XR device (or a server in communication with the XR device) may temporarily store (e.g., cache) bending data in association with the biometric data. For example, bending data may be stored in a cache component in association with a hand size calibration generated during a previous user session. It is important to note that any storing or saving of biometric data or bending data in this context is done on a temporary (non-persistent) basis and is anonymous in the sense that the data is not associated with an identifiable user profile, user name, or the like. In fact, examples described herein obviate the need to do so. Furthermore, and also indicated elsewhere, any bending data or biometric data collected by components described herein is captured or temporarily stored only with prior user approval and deleted on user request. Further, bending data and biometric data referred to herein is used for very limited purposes and strictly within the bounds of the user approval.

The "obtained" bending data referred to above may be first bending data and the bending data that is associated with the previously identified biometric data may be second bending data. In some examples, determining whether to use the previously identified biometric data in the tracking operation includes comparing the first bending data to the second bending data.

In some cases, the XR device may determine that the first bending data (e.g., bending data obtained in a current user session) matches the second bending data (e.g., bending data from a previous user session). Based on determining that the first bending data matches the second bending data, the XR device may identify that no calibration operation is required for the user, e.g., the XR device may identify that the biometric data already associated with the second bending data can be used to initialize or run the tracking operation. In such cases, the selected mode may be the first mode of the XR device in which previously identified biometric data is selected for use in the initializing or running of the tracking operation.

The previously identified biometric data that is associated with the bending data, e.g., a hand size calibration associated with a specific XR device bending, may be updated or adjusted. For example, the XR device may adjust the biometric data that it previously obtained during a subsequent tracking operation to enable the biometric data to be refined. The biometric data may be refined across multiple user sessions to improve tracking accuracy and/or speed of tracking initialization.

It is noted that the term "matching," as used herein in the context of a comparison between the first bending data and the second bending data, is not limited to identical matches. For example, the XR device may detect a match between the first bending data (e.g., from a previous user session) and the second bending data (obtained "live" during a current session) if they are in an acceptable bending range of each other. In some cases, where strain is measured to check bending, for example, the two sets of data may be deemed to match if the strain is more than 90% or more than 95% similar. In other cases, a VIO system of the XR device may be used to estimate bending. The first bending data as estimated using the VIO system may be compared to the second bending data as estimated using the VIO system and they may be determined to "match" if the second bending data does not differ from the first bending data by more than a threshold (e.g., a predetermined percentage). If there is no match, and as described elsewhere, a new calibration may then be required.

In some cases, if the first bending data matches the second bending data, the XR device may identify a current user of the XR device as corresponding to a previous user of the XR device. It is important to note that this is done without requiring identifying personal information, such as a user name or user profile. For example, the XR device may detect, based on the matching bending data alone, that the current user wearing the XR device is the same user for whom the XR device previously identified biometric data (e.g., a hand feature calibration) together with the second bending data during a previous user session. In this way, the XR device is able to load a previous calibration, obviating both the need to recalibrate and the need to identify a specific user (e.g., the user profile of the current user).

In some cases, the XR device may determine that the first bending data does not match the second bending data. Based on determining that the first bending data does not match the second bending data, the XR device may identify that a calibration operation is required for the user, e.g., the XR device may identify that the biometric data associated with the second bending data should not be used to initialize or run the tracking operation as it does not relate to the user currently wearing the XR device (again, without actually having to identify the user). In such cases, the selected mode may be the second mode of the XR device in which a calibration operation is performed for the user currently wearing the XR device.

In the second mode, the XR device may perform the calibration operation to obtain new biometric data for use in the tracking operation, e.g., a new hand feature calibration for hand tracking. The new biometric data may be associated with the first bending data (e.g., the "live" bending data obtained in the current user session).

If the first bending data does not match the second bending data, the XR device may identify that the current user of the XR device does not correspond to a previous user of the XR device. It is noted that the XR device may check multiple data items, e.g., multiple pairs of bending data with corresponding biometric data, for a match. In other words, the XR device may check details of bending data and corresponding biometric data for multiple different users (again, without actually having to identify or know the identity of the users).

Examples described herein thus enable the association of XR device bending information with calibrated features, such as calibrated hand sizes from different users, in a useful manner, and the use of the XR device bending information to retrieve such calibrated features. In some examples, the bending measurements obtained during different user sessions for the same user are approximately the same or sufficiently unique compared to bending measurements for other users. This enables an XR device to obviate the need for biometric calibration, e.g., hand size calibration, when the bending measurement matches a previous measurement, with calibration only becoming necessary when there is no match between a current bending measurement and one or more previous measurements.

Implementation of techniques described herein may address the technical problems of reducing computation time or computational load. For example, by using techniques described herein, less stereo matching may be required during or prior to hand tracking, thus reducing overall computation time and computational load. Examples of computing resources that may be saved include processor cycles, network traffic, memory usage, data storage capacity, power consumption, network bandwidth, or cooling capacity. Further, the XR device may be able to reduce a time delay experienced between the initialization of a tracking operation and a time when high tracking accuracy can be achieved.

Further, implementation of techniques described herein may address the technical problem of improving hand size estimates, e.g., by taking frames from different user sessions (possibly providing different lighting conditions, occlusions, hand poses, or the like) into account to refine a calibration. Examples described herein may provide improved initial hand alignment, e.g., by obviating the need to process a number of camera frames before being able to estimate hand size.

FIG. 1 is a network diagram illustrating a network environment 100 suitable for operating an XR device 110, according to some examples. The network environment 100 includes an XR device 110 and a server 112, communicatively coupled to each other via a network 104. The server 112 may be part of a network-based system. For example, the network-based system may be or include a cloud-based server system that provides additional information, such as virtual content (e.g., three-dimensional models of virtual objects, or augmentations to be applied as virtual overlays onto images depicting real-world scenes) to the XR device 110.

A user 106 operates the XR device 110. The user 106 may be a human user (e.g., a human being), a machine user (e.g., a computer configured by a software program to interact with the XR device 110), or any suitable combination thereof (e.g., a human assisted by a machine or a machine supervised by a human).

The user 106 is not part of the network environment 100, but is associated with the XR device 110. For example, where the XR device 110 is a head-wearable apparatus, the user 106 wears the XR device 110 during a user session. Although only one user 106 is shown in FIG. 1, the XR device 110 may be used (e.g., worn) by multiple different users during different user sessions.

The user 106 operates an application of the XR device 110, referred to herein as an AR application. The AR application may be configured to provide the user 106 with an experience triggered or enhanced by a physical object 108, such as a two-dimensional physical object (e.g., a picture), a three-dimensional physical object (e.g., a statue, a building, a person, or an animal), a location (e.g., at factory), or any reference points (e.g., perceived corners of walls or furniture, or Quick Response (QR) codes) in the real-world physical environment. For example, the user 106 may point a camera of the XR device 110 to capture an image of the physical object 108 and a virtual overlay may be presented over the physical object 108 via the display. Experiences may also be triggered or enhanced by a hand or other body part of the user 106, e.g., the XR device 110 may detect and respond to hand gestures.

The XR device 110 includes tracking components (not shown in FIG. 1). The tracking components track the pose (e.g., position, orientation, and location) of the XR device 110 relative to the real-world environment 102 using image sensors (e.g., depth-enabled 3D camera, and image camera), inertial sensors (e.g., gyroscope, accelerometer, or the like), wireless sensors (e.g., Bluetooth™ or Wi-Fi™), a Global Positioning System (GPS) sensor, and/or audio sensor to determine the location of the XR device 110 within the real-world environment 102.

In some examples, the server 112 may be used to detect and identify the physical object 108 based on sensor data (e.g., image and depth data) from the XR device 110, and determine a pose of the XR device 110 and the physical object 108 based on the sensor data. The server 112 can also generate a virtual object based on the pose of the XR device 110 and the physical object 108.

In some examples, the server 112 communicates a virtual object to the XR device 110. The XR device 110 or the server 112, or both, can also perform image processing, object detection and object tracking functions based on images captured by the XR device 110 and one or more parameters internal or external to the XR device 110. The object recognition, tracking, and AR rendering can be performed on either the XR device 110, the server 112, or a combination of the XR device 110 and the server 112. The server 112 may include or be communicatively coupled to a storage component that stores certain data relating to XR experiences.

While certain functions are described herein as being performed by either an XR device or a server, the location of certain functionality may be a design choice. For example, it may be technically preferable to deploy particular technology and functionality within a server system initially, but later to migrate this technology and functionality to a client installed locally at the XR device where the XR device has sufficient processing capacity.

The network 104 shown in FIG. 1 may be any network that enables communication between or among machines (e.g., server 112), databases, and devices (e.g., XR device 110). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

The XR device 110 may be a flexible device that is capable of bending to accommodate the body of the user 106, e.g., the XR device 110 may be AR glasses that deform to fit the head of the user 106. The geometry of the XR device 110 as initially calibrated (e.g., during manufacture, during another production process, or prior to sale) may therefore change during use. That is, when in use, the XR device 110 may be placed under conditions that are different from the conditions in which the XR device 110 was initially calibrated and that change, deform, or distort the geometry of the XR device 110. One of the situations in which the geometry of the XR device 110 components may be distorted is when the frame of the XR device 110 deforms as a result of use, either temporarily or permanently. For example, in order to be worn securely, users with different physical features may cause the frame of the XR device 110 to deform in different ways.

Figure 2:
FIG. 2 diagrammatically illustrates an XR device when not worn by a user, according to some examples.
Figure 2:
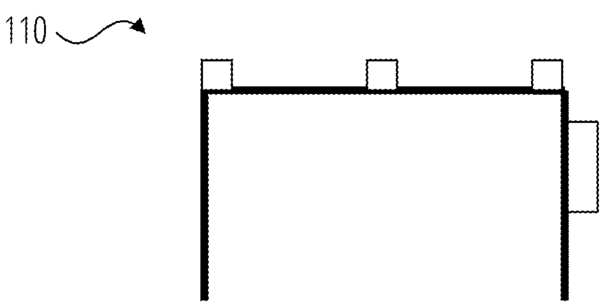
Figure 3:
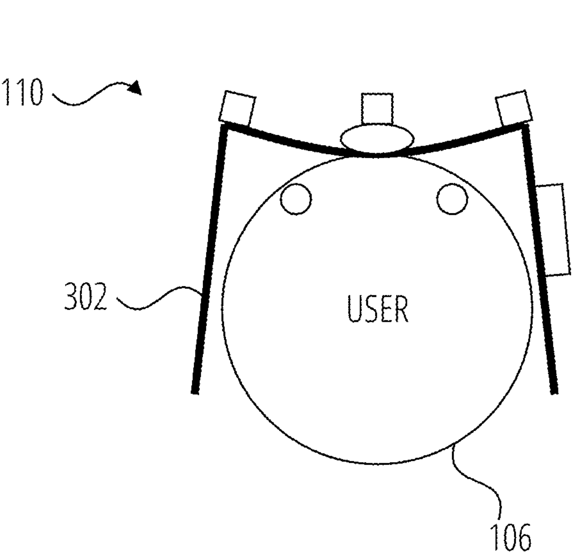
FIG. 3 diagrammatically illustrates the XR device of FIG. 2 when worn by a user, according to some examples.
Figure 3:

FIG. 2 and FIG. 3 diagrammatically illustrate bending of the XR device 110, according to some examples. In a diagram 200 of FIG. 2, the XR device 110 (according to some examples) is shown from above in a first condition in which it is not worn. In a diagram 300 of FIG. 2, the XR device 110 (according to some examples) is shown from above in a second condition, or an "in use" condition, in which it is worn by the user 106.

It will be evident from FIG. 3 that the XR device 110 bends to accommodate the head of the user 106. More specifically, a frame 302 of the XR device 110 bends, resulting in relative spatial changes in components mounted to the frame 302, as is diagrammatically illustrated in FIG. 3. Sides of the XR device 110 may be thrust forward, changing the geometry of the XR device 110, e.g., as a result of the shape, proportion, size and other aspects of the user's head and/or other physiological characteristics of the user. The bending may become more pronounced if the frame 302 is made of material that is easy to bend.

In bending, it is noted that the bending of the frame 302 may follow certain rules. For example, when the frame 302 bends, it may form a continuous curve, bend symmetrically from the middle to the ends of a front region, or follow some other bending "rule." Bending may be controlled by design, at least to some extent, as opposed to occurring in a random fashion. Bending, whether or not it occurs symmetrically, smoothly, or evenly, may be modeled, estimated, or measured, allowing the XR device 110 to capture or collect bending data relating to a specific user when the user is wearing the XR device 110.

Where the XR device 110 is a flexible device, it may therefore use one or more sensors to collect, obtain, or analyze bending data. The XR device 110 may use a dedicated bending sensor or may use an object tracking system for this purpose. As described further below, estimates of the bending of the XR device 110, e.g., the frame, can then be collected and used to generate bending data. Bending data may be unique to the user 106 wearing the flexible device.

Figure 4:
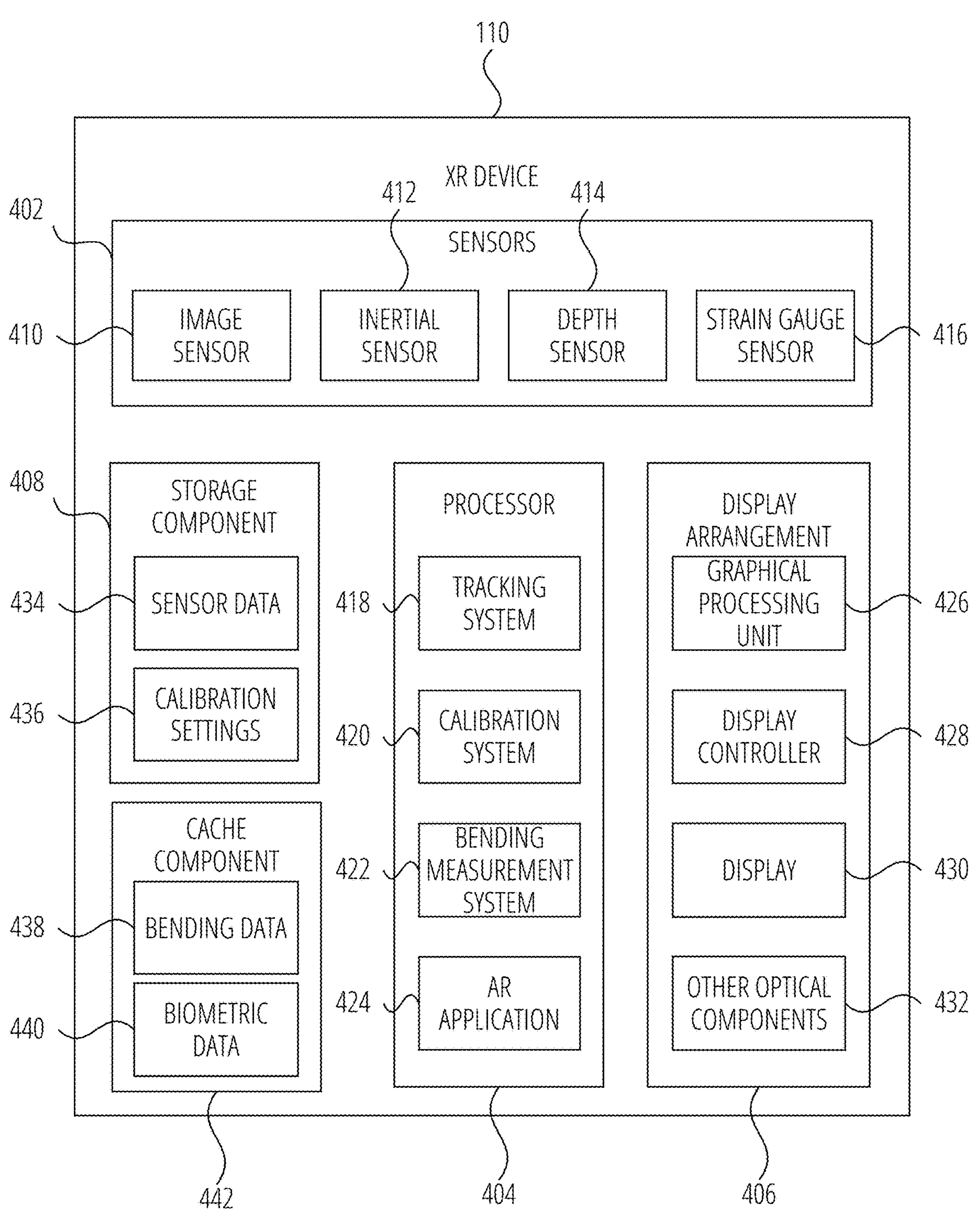
FIG. 4 is a block diagram illustrating components of an XR device, according to some examples.

FIG. 4 is a block diagram illustrating components (e.g., parts, modules, or systems) of the XR device 110, according to some examples. The XR device 110 includes sensors 402, a processor 404, a display arrangement 406, a storage component 408, and a cache component 442.

It will be appreciated that FIG. 4 is not intended to provide an exhaustive indication of components of the XR device 110. Further, one or more of the components described herein may be implemented using hardware (e.g., a processor of a machine) or a combination of hardware and software. For example, a component described herein may configure a processor to perform the operations described herein for that component. Moreover, two or more of these components may be combined into a single component, and the functions described herein for a single component may be subdivided among multiple components. Furthermore, according to various examples, components described herein as being implemented within a single machine, database, or device may be distributed across multiple machines, databases, or devices.

The sensors 402 include one or more image sensors 410, one or more inertial sensors 412, and one or more depth sensors 414. In some examples, and as shown in FIG. 4, the sensors 402 include one or more strain gauge sensors 416. However, these are merely examples and other configurations are possible. For example, the XR device 110 may perform techniques described herein without depth sensors and strain gauges, at least in some examples.

The image sensor 410 may include, for example, a combination of a color camera, a thermal camera, a depth sensor, and one or multiple grayscale, global shutter tracking cameras. The inertial sensor 412 may include a combination of a gyroscope, accelerometer, and a magnetometer. In some examples, the inertial sensor 412 includes one or more IMUs. An IMU is a sensor or device that can report on the inertial status of a moving body, including one or more of the acceleration, velocity, orientation, and position of the moving body. In some examples, an IMU enables tracking of movement of a body by integrating the acceleration and the angular velocity measured by the IMU. An IMU can have a combination of accelerometers and gyroscopes that can determine and quantify linear acceleration and angular velocity, respectively. The values obtained from one or more gyroscopes of an IMU can be processed to obtain data including the pitch, roll, and heading of the IMU and, therefore, of the body with which the IMU is associated. Signals from one or more accelerometers of the IMU also can be processed to obtain data including velocity and/or displacement of the IMU and, therefore, of the body with which the IMU is associated.

The depth sensor 414 may include one or more of a structured-light sensor, a time-of-flight sensor, passive stereo sensor, and an ultrasound device. The strain gauge sensor 416 may be used to measure the force being applied to the XR device 110. For example, where the XR device 110 is a head-worn device, the strain gauge sensor 416 measures the force applied by a head of the user 106 to the XR device 110 by measuring deformation of a frame of the XR device 110, and sends signals indicating its measurements to the processor 404.

Other examples of sensors 402 include a proximity or location sensor (e.g., near field communication, GPS, Bluetooth™, or Wi-Fi™), an eye tracking sensor (e.g., to monitor gaze direction), an audio sensor (e.g., a microphone), or any suitable combination thereof. It is noted that the sensors 402 described herein are for illustration purposes and the sensors 402 are thus not limited to the ones described above.

The processor 404 executes or implements one or more of a tracking system 418, a calibration system 420, a bending measurement system 422, and an AR application 424.

The tracking system 418 is responsible for tracking the XR device 110 itself and for tracking objects relative to the XR device 110. The tracking system 418 may use a SLAM system and/or VIO system to estimate a pose (position and orientation) of the XR device 110 and continuously updates the estimated pose. For example, the tracking system 418 uses image data from the image sensor 410 and inertial data from the inertial sensor 412 to track a location or pose of the XR device 110 relative to a frame of reference (e.g., real-world environment 102 as shown in FIG. 1). The tracking system 418 may use images of the user's real-world environment 102, as well as other sensor data to identify a relative position and orientation of the XR device 110 from physical objects in the real-world environment 102 surrounding the XR device 110.

In some examples, the tracking system 418 uses the sensor data to determine the pose of the XR device 110 along six degrees of freedom, also referred to as "6DOF." In the context of an XR device, 6DOF pose tracking may refer to the tracking of the pose of an object along three degrees of translational motion and three degrees of rotational motion.

The tracking system 418 may be used to build a map of the real-world environment and to locate the XR device 110 within the real world. This facilitates, for example, accurate placement of virtual content overlaid, or superimposed, on the real world and tracking of their position as a user moves and/or as objects move. The VIO system combines data from the inertial sensor 412 and the image sensor 410 to estimate the position and orientation of an object in real-time. The tracking system 418 may provide the pose of the XR device 110 to the display arrangement 406.

The tracking system 418 may allow for the detection and tracking of an object, e.g., the physical object 108 or a feature of the user 106 of the XR device 110, such as the hand of the user 106. The tracking system 418 may include a computer-operated application or system that enables a device or system to detect and track visual features identified in images captured by the image sensor 410. The tracking system 418 may implement one or more object tracking machine learning models to track an object, e.g., an object traveling in the field of view of a user during a user session.

In some examples, during operation, the image sensor 410 captures video frames of the real-world environment 102. The frames are then processed by the tracking system 418 to extract visual features or other information using one or more computer vision techniques. Examples of such techniques include template matching, edge detection, and feature point extraction. In some examples, the image sensor 410 may include multiple cameras arranged to increase an overall field of view and provide overlapping coverage. The tracking system 418 may employ stereo matching techniques to facilitate or provide depth estimation.

The tracking system 418 may implement two phases of object tracking: a detection phase in which the object of interest (e.g., a hand or a person in the camera field of view) is identified, and a tracking phase in which the pose of the object is tracked over a period of time, e.g., to detect hand gestures. Various algorithms, including algorithms implemented by object tracking machine learning models, may be used to predict or estimate the movement or pose of the object and to update the pose of the object over time.

An object tracking machine learning model may comprise a neural network trained on suitable training data to identify and track objects in a sequence of frames captured by the XR device 110. The machine learning model may be applied to track the movement of an object in a sequence of images or videos. It typically uses an object's appearance, motion, landmarks, and/or other features to estimate location in subsequent frames.

The calibration system 420 is used to calibrate the tracking system 418 for a specific set of features. For example, when the tracking system 418 performs hand tracking, the calibration system 420 calibrates the tracking system 418 by using a hand calibration, e.g., a hand size calibration.

The calibration system 420 is responsible for performing one or more calibration steps to measure or estimate hand features, e.g., the size of a hand and/or details of hand landmarks (e.g., fingers and joints). Different types of calibration operations may be performed.

In a first example type of calibration, the calibration system 420 performs calibration when the XR device 110 is initially being set up for operation. The first example type of calibration may be referred to as "offline" calibration. This type of calibration may be relatively inflexible, particularly where the XR device 110 is to be used by multiple users. Further, this first type of calibration may require the storing or association of biometric data (e.g., hand size) with a specific user profile, which may in turn have undesirable privacy or security implications.

In a second example type of calibration, the calibration system 420 performs calibration during operation, e.g., during an AR user session. This second example type of calibration may be referred to as an "online" or "live" calibration step. When performing this second type of calibration, one or more of the sensors 402 are used to calibrate the tracking system 418 while a user session is in progress, e.g., to estimate hand size and adjust the tracking system 418 based on the hand size. As mentioned, examples described herein obviate the need for the first example type of calibration.

Referring now specifically to hand feature calibration, the calibration system 420 may estimate certain hand features (e.g., certain bone lengths) by using depth information from a depth sensor (e.g., the depth sensor 414) and/or images of the hand captured from different angles (e.g., by multiple cameras of the image sensor 410) or points in time.

For example, each hand may be represented as a set of bones connected in a tree-like structure. Each bone can be defined as the connection between two landmarks. The calibration system 420 may compute a 3D model of the hand in a certain rest pose, where the goal is to estimate the actual lengths of one or more bones of the user and so constrain the optimization problem for the tracking system 418 that tries to predict the pose of each bone as accurately and efficiently as possible. The calibration system 420 may work with multiple components of XR device 110, such as the tracking system 418, to detect the hand, crop images to focus on the hand (e.g., by cropping a bounding box), detect 2D landmarks, find corresponding 2D landmarks in one or more different camera images, and by using camera and lens parameters, triangulate the 2D points to obtain depth and 3D coordinates of the various landmarks.

In some examples, the calibration system 420 utilizes a reference bone length to increase accuracy of the estimations for the landmarks. For example, the size of the hand can be estimated or predicted by using a length of a reference bone (e.g., a metacarpal bone) and applying triangulation to determine positions of one or more other 3D landmarks (e.g., joints).

Techniques such as those described above allow the calibration system 420 to compute or estimate the actual length of the bones and generate a hand feature calibration, e.g., in the form of a 3D hand model. Accordingly, the previously identified biometric data referred to herein may, in some examples, be, include, or be associated with a previously obtained 3D hand model.

Once a hand feature calibration such as a 3D hand model has been created, it may be used as a reference or constraint for hand tracking. For example, as the user 106 moves their hand, the XR device 110 captures new images and uses the constraint to estimate the hand's movement and pose in 3D space, allowing the XR device 110 to understand hand gestures and overlay virtual objects relative to the hand.

The hand feature calibration may be used to calibrate a hand tracking component of the tracking system 418. For example, the hand feature calibration may be used to adjust parameters of a tracking algorithm of the tracking system 418 to account for the size of the user's hand. In some examples, a final hand feature calibration may consist of a set of parameters that describe the user's hand size (and/or other data points of the hand) and how it affects the tracking algorithm.

Traditional calibration performed using the second example type of calibration referred to above, e.g., calibration performed during an AR user session, may increase computational cost as calibration is needed for each new user session. Further, in traditional calibration, there may be a delay during runtime when performing hand calibration, as hand features are usually estimated from a plurality of observations (e.g., a series of frames) over a period of time. For example, calibration may be performed for a period of time until hand size estimates converge to an acceptable point or extent. Examples described herein address or alleviate these technical challenges by associating bending data with biometric data, e.g., hand feature calibrations, as further described below.

Referring now to the bending measurement system 422 shown in FIG. 4, the bending measurement system 422 is used to facilitate or perform the measurement or estimation of bending of the XR device 110 to accommodate the relevant body part or body parts of the user 106. The bending measurement system 422 may generate bending data which describes or defines the bending of the relevant body part of body parts.

Several techniques may be used to measure or estimate bending. In some examples, the strain gauge sensor 416, e.g., a linear strain gauge sensor or combination of linear strain gauge sensors (e.g., in 2 or 3 axes), may be used to generate measurements indicative of strain caused by the force applied by the head of the user 106 to the frame of the XR device 110. For example, the strain gauge sensor 416 (or sensors) may measure deformation of the frame. The strain gauge measurement may itself be used (directly) as bending data or may be converted to a bending value. For example, the bending measurement system 422 may determine, based on a predetermined calibration or transformation, that the measurement received from the strain gauge sensor 416 indicates a 1-degree bend or a 5-degree bend in a frame of the XR device 110, and this bending value may be used as the bending data.

In some examples, computer vision techniques may be used to estimate bending. The tracking system 418 may operate on stereo vision using two or more cameras of the image sensors 410 that are mounted on the XR device 110. For example, one camera is mounted to or near a left temple of a frame of the XR device 110 and another camera is mounted to or near a right temple of the frame of the XR device 110. Stereo vision can be used to detect a degree of bending of the XR device 110.

For example, during operation, the cameras may be in a modified orientation with respect to one another due to bending of the XR device 110 (e.g., the frame). A computer vision algorithm of the bending measurement system 422 or tracking system 418 may then determine a bending value based on the triangulation of features in the captured images (e.g., the bending measurement system 422 may determine that there is a 1-degree or a 5-degree bend in the frame).

In some examples, the cameras may produce images that overlap, with a baseline overlap being defined during manufacture. During operation, the cameras may then be in a modified orientation with respect to one another due to bending of the XR device 110 (e.g., the frame). A computer vision algorithm of the bending measurement system 422 or tracking system 418 may then determine a bending value based on the difference between the modified overlap and the baseline overlap, e.g., the bending measurement system 422 may determine that there is a 1-degree or a 5-degree bend in the frame. The bending measurement system 422 may determine a bending value as a function of the overlap.

In some examples, a computer vision algorithm may use a VIO system of the tracking system 418 to sample points in images and estimate bending based on a sequence of stereo frames. In some examples, a depth map may be generated using VIO data, based on the depth of matched features between a left image (generated by a left side camera) and a right image (generated by a right side camera). The computer vision algorithm may then analyze the depth map, e.g., by checking disparities, to estimate the bending of the XR device 110.

Accordingly, it will be appreciated that various techniques and/or components may be used to determine bending to allow the XR device 110 to obtain the bending data referred to herein.

The AR application 424 may retrieve a virtual object (e.g., 3D object model) based on an identified physical object 108 or physical environment (or other real-world feature), or retrieve an augmentation to apply to the physical object 108. A graphical processing unit 426 of the display arrangement 406 causes display of the virtual object, augmentation, or the like. The AR application 424 may include a local rendering engine that generates a visualization of a virtual object overlaid on (e.g., superimposed upon, or otherwise displayed in tandem with) an image of the physical object 108 (or other real-world feature, e.g., the hand of the user 106) captured by the image sensor 410. A visualization of the virtual object may be manipulated by adjusting a position of the physical object or feature (e.g., its physical location, orientation, or both) relative to the image sensor 410. Similarly, the visualization of the virtual object may be manipulated by adjusting a pose of the XR device 110 relative to the physical object or feature.

A display 430 of the display arrangement 406 may include a screen or panel configured to display images generated by the processor 404 or the graphical processing unit 426. In some examples, the display 430 may be transparent or semi-transparent so that the user 106 can see through the display 430. Referring again to the graphical processing unit 426, the graphical processing unit 426 may include a render engine that is configured to render a frame of a 3D model of a virtual object based on the virtual content provided by the AR application 424 and the pose of the XR device 110 (and, in some cases, the position of a tracked object as modified or adjusted by calibration data).

In other words, the graphical processing unit 426 may use the three-dimensional pose of the XR device 110 to generate frames of virtual content to be presented on the display 430. For example, the graphical processing unit 426 uses the three-dimensional pose to render a frame of the virtual content such that the virtual content is presented at an orientation and position in the display 430 to properly augment the user's reality. As an example, the graphical processing unit 426 may use the three-dimensional pose data to render a frame of virtual content such that, when presented on the display 430, the virtual content is caused to be presented to a user so as to overlap with a physical object in the user's real-world environment 102. The graphical processing unit 426 can generate updated frames of virtual content based on updated three-dimensional poses of the XR device 110 and updated tracking data generated by the abovementioned tracking components, which reflect changes in the position and orientation of the user in relation to physical objects in the user's real-world environment 102, thereby resulting in a more immersive experience.

The graphical processing unit 426 may transfer a rendered frame to a display controller 428 of the display arrangement 406. The display controller 428 is positioned as an intermediary between the graphical processing unit 426 and the display 430, receives the image data (e.g., rendered frame) from the graphical processing unit 426, re-projects the frame (e.g., by performing a warping process) based on a latest pose of the XR device 110 (and, in some cases, based on object tracking pose forecasts or predictions), and provides the re-projected frame to the display 430. The display arrangement 406 may include several other optical components 432, such as lenses, mirrors, or waveguides.

It will be appreciated that, in examples where an XR device includes multiple displays, each display may have a dedicated graphical processing unit and/or display controller. It will further be appreciated that where an XR device includes multiple displays, e.g., in the case of AR glasses or any other AR device that provides binocular vision to mimic the way humans naturally perceive the world, a left eye display arrangement and a right eye display arrangement may deliver separate images or video streams to each eye. Where an XR device includes multiple displays, steps may be carried out separately and substantially in parallel for each display, in some examples, and pairs of features or components may be included to cater for both eyes.

The storage component 408 may store various data, such as sensor data 434, and calibration settings 436. The sensor data 434 may include data captured or obtained by the sensors 402, e.g., captured images, IMU data, depth information, or strain gauge readings. The calibration settings 436 may include settings or rules to be followed in performing calibration for purposes of a tracking operation, e.g., settings or rules for performing hand feature calibration for a hand tracking operation. The calibration settings 436 may define multiple modes of the XR device 110 or govern when the XR device 110 should enter a specific mode. As described further below, in one mode, the XR device 110 may use previously identified biometric data (e.g., a hand size calibration) to initialize or run the tracking operation, while in another mode, the XR device 110 may perform calibration to obtain new biometric data (e.g., a new hand size calibration) to initialize or run the tracking operation.

Certain data, such as bending data 438 and biometric data 440, may be stored temporarily (e.g., non-persistently) in the cache component 442 of the XR device 110. The bending data 438 may include bending data estimated or measured during a user session. The biometric data 440 may include biometric data of a user measured or obtained during a user session. For example, the biometric data 440 may include a hand feature calibration, such as a hand size estimate or 3D hand model. Bending data and biometric data from the same user session may be cached in association with one another in the cache component 442 to allow biometric data to be retrieved based on bending data, as described further below. The cache component 442 may cache multiple "bending-biometric" pairs, e.g., a first bending-biometric pair may be the bending data and the corresponding hand size calibration of a first user obtained during a first user session, a second bending-biometric pair may be the bending data and the corresponding hand size calibration of a second user obtained during a second user session, and so forth.

It is noted that the bending measurement system 422 may estimate bending over a period of time (e.g., every minute) and the bending data may thus be updated over time to reflect changes in bending values. Similarly, the calibration system 420 may adjust or refine calibrations over time and the biometric data may thus also be updated.

Figure 5:
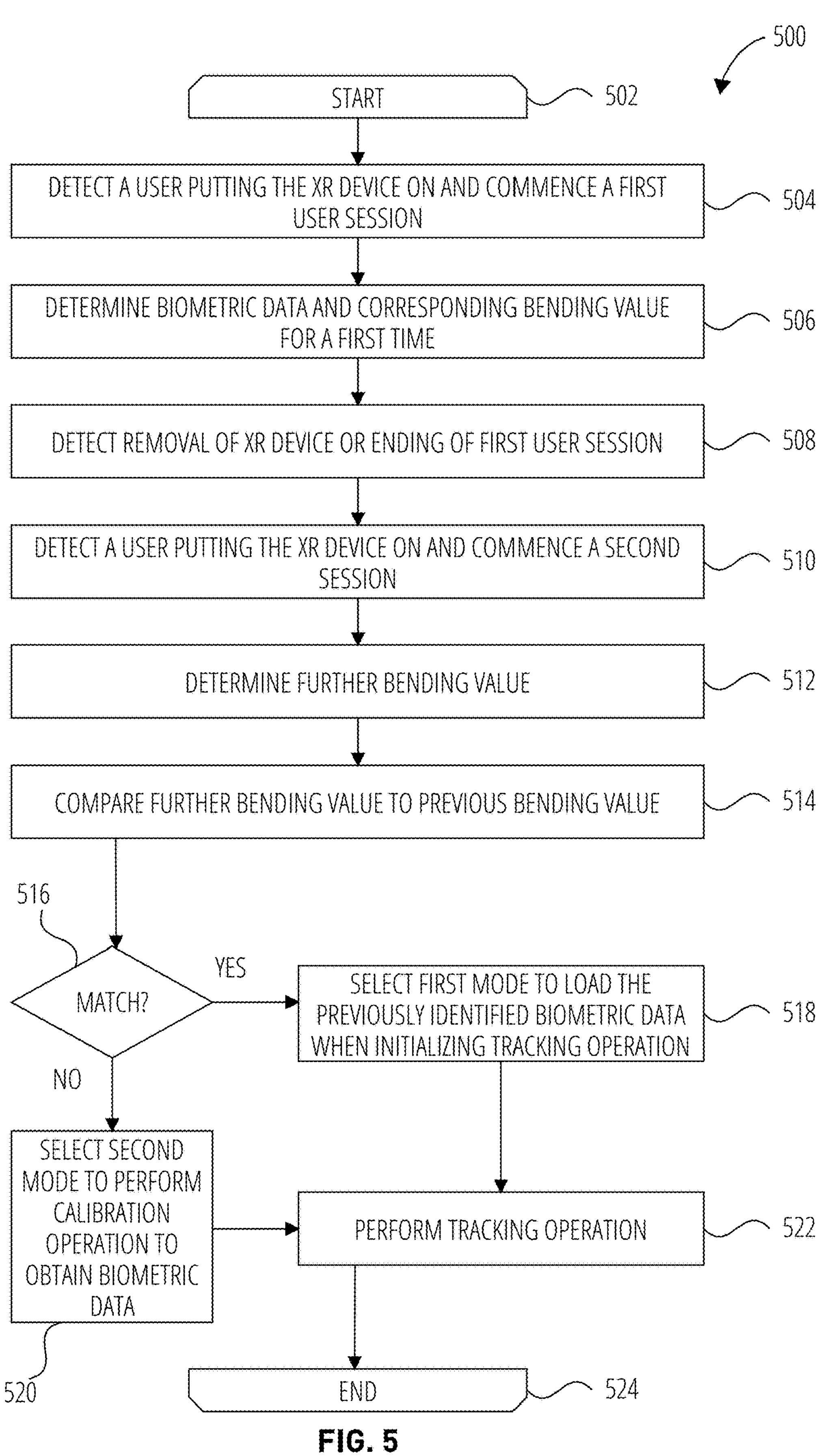
FIG. 5 is a flowchart illustrating a method suitable for analyzing bending data to determine whether to use previously identified biometric data in a tracking operation of an XR device, according to some examples.

FIG. 5 is a flowchart illustrating a method 500 suitable for analyzing bending data to determine whether to use previously identified biometric data in a tracking operation of an XR device, according to some examples. Operations in the method 500 may be performed by the XR device 110 using components (e.g., parts, modules, systems, or engines) described above with respect to FIGS. 1 and 4. Accordingly, by way of example and not limitation, the method 500 is described with reference to the XR device 110 and certain components thereof.

In the method 500, the XR device 110 is a head-wearable device, e.g., AR glasses. Further, in the method 500, the tracking operation is a hand tracking operation. However, it will be appreciated that similar techniques may be applied with respect to other types of XR devices or other types of tracking operations, e.g., the tracking of other features, such as other body parts, of a user.

The method 500 commences at opening loop element 502 and proceeds to operation 504, where the XR device 110 detects that a user has put the XR device 110 on. For example, the sensors 402 of the XR device 110 may include one or more of a proximity sensor, capacitive sensor, IMU or infrared sensor to automatically detect that the user is wearing the XR device 110. The XR device 110 may initiate a new user session responsive to detecting that the user has put the XR device 110 on or responsive to a user input, e.g., responsive to the user switching the XR device 110 on or selecting the AR application 424.

In the method 500 of FIG. 5, a first user puts the XR device 110 on for a first time and the user session of operation 504 is therefore the first user session of the particular user. At operation 506, while the first user session is in progress, the XR device 110 uses the calibration system 420 and the tracking system 418 to estimate the hand size of the first user and to calibrate the tracking system 418 for the estimated hand size. As mentioned above, this may involve generating a 3D hand model.

Further, the XR device 110 uses the bending measurement system 422 to measure or estimate the bending of the XR device 110 caused by the head of the first user, thus yielding bending data. The XR device 110 associates the relevant biometric data, which in this case includes a hand feature calibration of the user, with the bending data for the same user. As mentioned above, the data are associated with each other without any information that reveals the identity of the specific user, e.g., not associated with a user profile or user name.

The XR device 110 subsequently, at operation 508, detects removal of the XR device 110 or ending of the first user session. The XR device 110 may use the abovementioned sensors to detect that the first user has removed the XR device 110 and automatically terminate the first user session. Alternatively, the first user session may be manually terminated, e.g., the first user may close the AR application 424 or switch off the XR device 110.

At operation 510, the XR device 110 again detects that a user has put the XR device 110 on and a second user session commences. The user of operation 510 may be the first user or a second user, as explained below. For example, no specific user identity or user profile may be loaded or linked to the second user session and the XR device 110 may thus, at the time when operation 510 commences, have insufficient data to associate the user currently wearing the XR device 110 with a particular identity.

While the second user session is in progress, the XR device 110 uses the bending measurement system 422 to measure or estimate the bending of the XR device 110 caused by the head of the current user, thus yielding further bending data (operation 512). The XR device 110 compares the further bending data with the bending data from the first user session, at operation 514, and determines whether the further bending data matches the bending data from the previous session (decision operation 516).

If the XR device 110 determines at decision operation 516 that the further bending data matches the bending data from the previous session, the previously identified biometric data (e.g., the hand feature calibration already generated by the XR device 110) is loaded at operation 518 (e.g., from the cache component 442 of FIG. 4) and used to initialize or run the hand tracking operation. The XR device 110 may thus determine, based on XR device bending and without having access to a user identity or user profile, that the user who put the XR device 110 on at operation 510 is the first user (who also put the XR device 110 on at operation 504). Operation 518 may thus involve selecting a first mode of the XR device 110 in which the previously identified biometric data is used to initialize or run the hand tracking operation.

The XR device 110 then performs hand tracking by using the hand feature calibration, (e.g., hand size, hand model, tracking algorithm parameters, or combinations thereof) for the first user at operation 522. This enables the XR device 110 to load a previous hand calibration and initialize hand tracking more quickly. This may also enable the XR device 110 to save computational resources, such as those required for stereo matching.

On the other hand, if the XR device 110 determines at decision operation 516 that the further bending data does not match the previous bending data, the previously identified biometric data is not loaded or used. Instead, the XR device 110 selects a second mode to perform a "fresh" calibration, e.g., hand size calibration, to obtain new biometric data with which to initialize the hand tracking operation (operation 520). The XR device 110 may thus determine, based on a mismatch in XR device bending and without having access to a user identity or user profile, that the user who put the XR device 110 on at operation 510 is not the first user, but rather a second user. The XR device 110 then performs hand tracking by using the new hand feature calibration for the second user at operation 522. The method 500 concludes at closing loop element 524.

As mentioned above, object tracking may involve two phases: a detection phase and a tracking phase. In the case of hand tracking, the XR device 110 detects or identifies the hand (or hands) of the user during the detection phase, after which the XR device 110 transitions to the tracking phase to track the movement or pose thereof.

As mentioned above, traditional calibration may require calibration to be performed during each user session. For example, and particularly when the XR device 110 does not have access to user-identifying information, such as a user profile, the tracking system 418 may need to be recalibrated for each user session by measuring or estimating the hand size (or other hand features) of the current user. In each user session, after the detection phase has been completed, the XR device 110 may perform hand calibration during a first part of the tracking phase. During this first part of the tracking phase, tracking may be relatively slow or inaccurate, given that hand features are still unknown.

After calibration, and during a second part of the tracking phase, the XR device 110 may then be able to perform faster or more accurate hand tracking (provided that the features of the hand were measured or estimated relatively accurately). When the user removes the XR device 110 and puts it on again, or when a first user session ends and a new one begins, the XR device 110 then has to repeat the detection phase and the tracking phase, including the first part of the tracking phase in which calibration is required.

Figure 6:
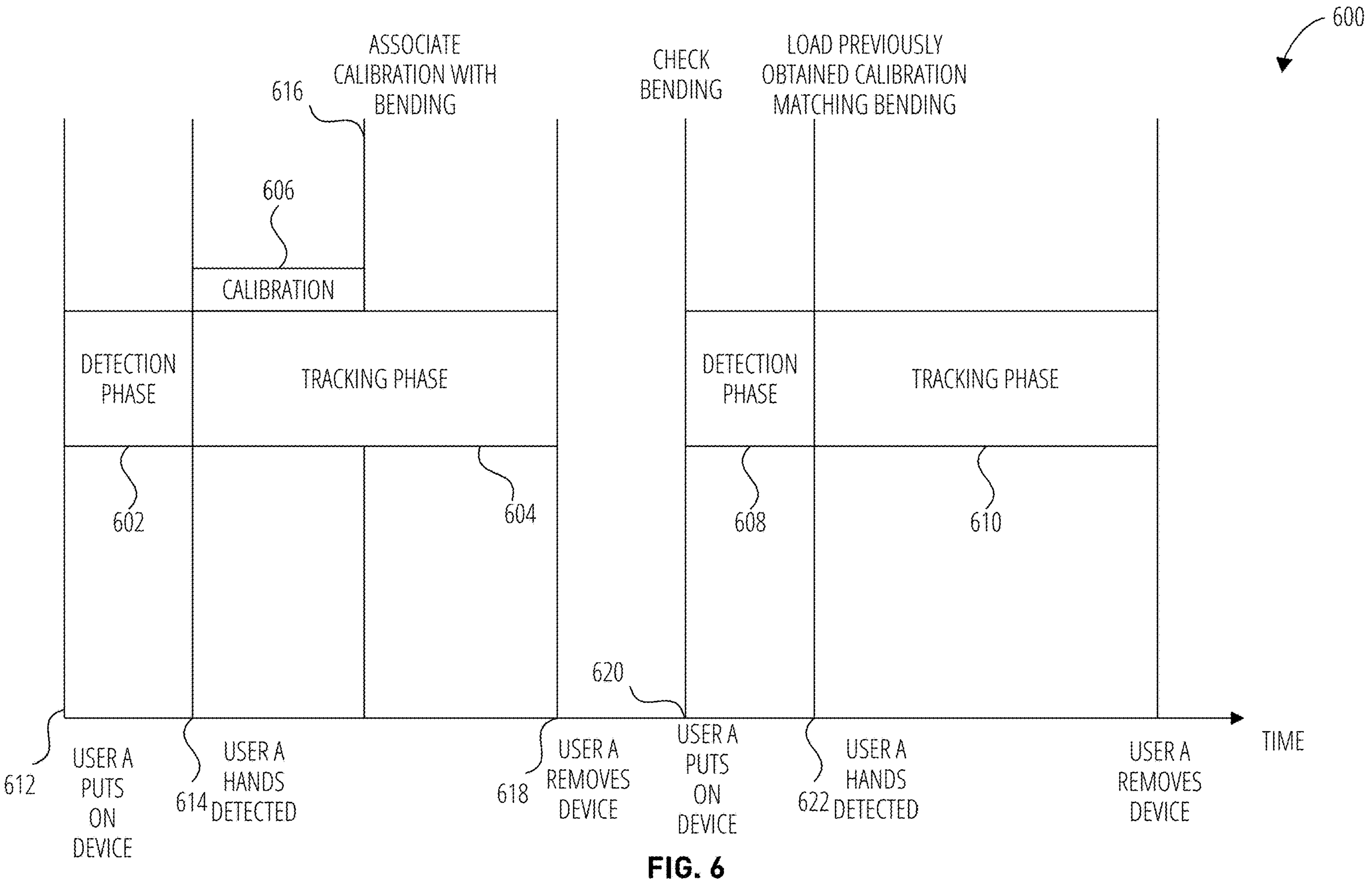
FIG. 6 diagrammatically illustrates detection and tracking phases in which an XR device uses a previously obtained hand calibration to facilitate one of the tracking phases, according to some examples.
Figure 7:
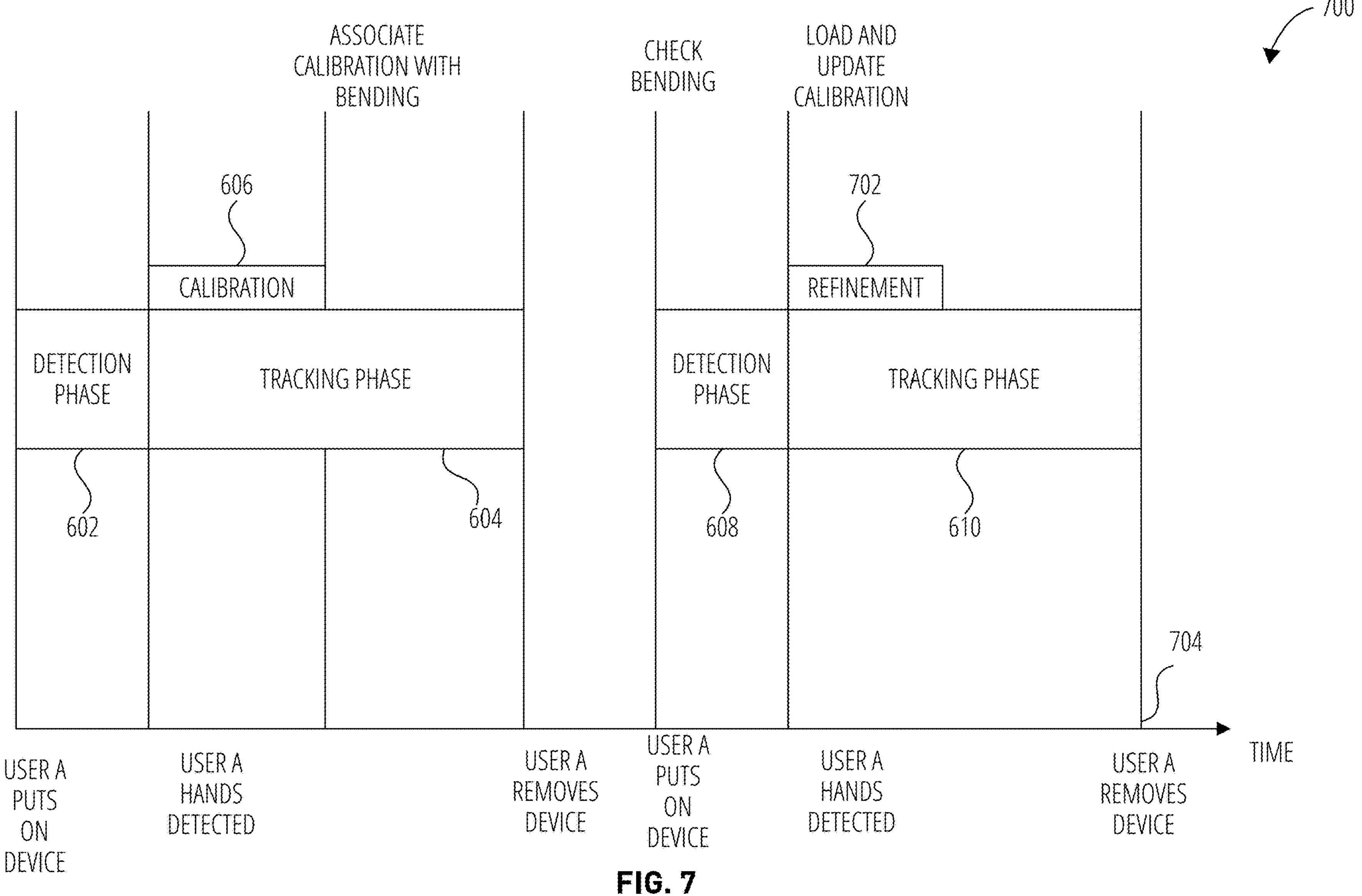
FIG. 7 diagrammatically illustrates detection and tracking phases in which an XR device uses a previously obtained hand calibration of a first user to facilitate one of the tracking phases and refines hand calibration across multiple user sessions, according to some examples.
Figure 8:
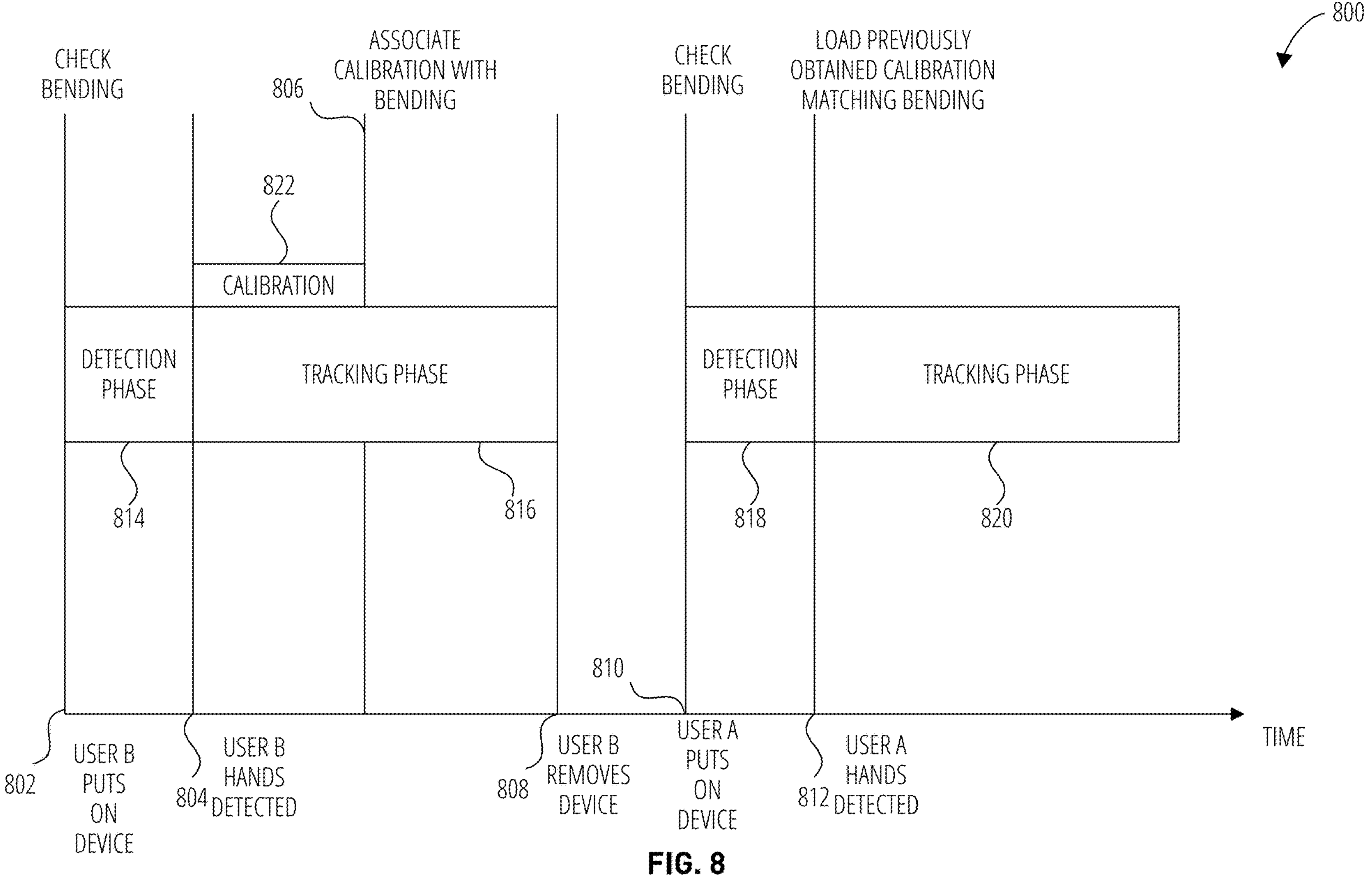
FIG. 8 diagrammatically illustrates detection and tracking phases in which the XR device of FIG. 7 performs hand calibration for a second user and subsequently uses the previously obtained hand calibration of the first user to facilitate the tracking phase for the first user, according to some examples.

FIGS. 6-8 show sequence diagrams 600, 700, and 800, respectively, each illustrating detection and tracking phases. Operations in the sequence diagrams 600, 700, and 800 may be performed by the XR device 110 using components (e.g., parts, modules, systems, or engines) described above with respect to FIGS. 1 and 4. Accordingly, by way of example and not limitation, the sequence diagrams 600, 700, and 800 are described with reference to the XR device 110 and certain components thereof.

Referring firstly to FIG. 6, the sequence diagram 600 shows detection and tracking phases in which the XR device 110 uses a previously obtained hand calibration to facilitate one of the tracking phases, according to some examples. At a first point in time 612, a user ("User A") puts on the XR device 110 and a detection phase 602 commences. At a second point in time 614, once the hands of the user have been detected, the XR device 110 starts a tracking phase 604. As described above, a first part of the tracking phase 604 involves calibration 606, allowing the XR device 110 to estimate the hand size of the user (e.g., to create a 3D hand model) and calibrate the tracking system 418 for hand tracking.

At a third point in time 616, once the calibration 606 has been completed, a second part of the tracking phase 604 starts. The XR device 110 is typically able to perform faster and more accurate tracking during the second part of the tracking phase 604, given that the hand calibration can be used for hand tracking (while not yet available in the first part of the tracking phase 604). Further, after the calibration 606 has been completed, the XR device 110 associates the hand calibration generated during the session with bending data indicative of the bending of the XR device 110 while worn by the user during the same session. The bending of the XR device 110 may be measured or estimated using a suitable technique, such as one of the techniques described with reference to FIG. 4.

At a fourth point in time 618, the user removes the XR device 110. At a fifth point in time 620, the same user then puts the XR device 110 on again. The XR device 110 detects the hands of the user during the detection phase 608 and checks the bending of the XR device 110. The XR device 110 determines that the bending matches the previous bending data and thus, at a sixth point in time 622, loads the previously generated hand calibration. Accordingly, the XR device 110 selects, or adjusts to, the first mode in which previously identified biometric data is used to facilitate tracking.

The previously generated hand calibration is used to initialize and run the tracking phase 610. Given that the XR device 110 does not need to calibrate or recalibrate the tracking system 418 based on a new set of biometric data, the delay caused by the calibration 606 in the tracking phase 604 is obviated or reduced, and the XR device 110 can more rapidly start performing quick and accurate hand tracking during the tracking phase 610. For example, in the tracking phase 604, the XR device 110 may only be able to start using the hand calibration from the third point in time 616, while in the tracking phase 610 the XR device 110 may be able to start using the hand calibration closer to the start of the tracking phase 610.

Referring now to FIG. 7, the sequence diagram 700 of FIG. 7 is the same as the sequence diagram 600, but for the addition of a calibration refinement operation 702 during the tracking phase 610. As mentioned, the XR device 110 may refine its previously generated hand calibration across multiple user sessions or multiple tracking phases to improve, for example, a 3D hand model and the corresponding tracking algorithm parameters.

Accordingly, in the sequence diagram 700 of FIG. 7, while the XR device 110 does not recalibrate the hand calibration obtained during the tracking phase 604, it may adjust or improve the hand calibration and update it accordingly during the calibration refinement operation 702. In other words, the XR device 110 may still save time and improve accuracy by reusing the calibration from the tracking phase 604 in the tracking phase 610, but can at the same time refine this calibration.

It may be advantageous to perform the calibration refinement operation 702 during one or more sessions to obtain more robust or accurate calibrations or improve estimate convergence. For example, hand features may be estimated during an initial part of the tracking phase (e.g., calibration 606) based on an initial set of images. If the hand appears relatively clearly in these images, it is typically possible to obtain accurate estimates. However, the initial set of images may be problematic, e.g., images may be blurry or have poor exposure, images may have poor lighting, images may contain occlusions, one or both hands may not be fully in the camera field of view, or a hand may be in a pose that is difficult to assess, leading to inaccurate estimates and thus reducing tracking quality.

If additional images are assessed during subsequent sessions in which the hands can be more accurately analyzed, the initial hand calibration may be refined. Accordingly, taking samples (e.g., stereo image samples) from multiple sessions can improve the overall quality of a hand calibration. This enables the XR device 110 to adjust its calibration over time to better match a user's hand, e.g., to better match the size of the hand to allow for improved gesture detection.

The sequence diagram 700 of FIG. 7 ends at an end point 704 when the user session of "User A" concludes, thus also ending the tracking phase 610. Turning to FIG. 8, the sequence diagram 800 continues from the sequence diagram 700 of FIG. 7. After the end point 704 of the first user session of the first user ("User A"), a second user ("User B") puts on the XR device 110 and a second user session commences at a first point in time 802 of the sequence diagram 800. In other words, a user switch occurs between the end point 704 of the sequence diagram 700 and the first point in time 802 of the sequence diagram 800.

At the first point in time 802, the XR device 110 starts a detection phase 814 to detect the hands of the second user. The XR device 110 also checks the bending of the XR device 110 and determines that the current bending does not match previous bending data. At a second point in time 804, once the hands of the second user have been detected and responsive to detecting that there is no matching bending data, the XR device 110 starts a tracking phase 816 that involves calibration 822, allowing the XR device 110 to estimate the hand size of the second user and calibrate the tracking system 418 for hand tracking. Accordingly, the XR device 110 selects, or adjusts to, the second mode in which previously identified biometric data is not used to facilitate tracking.

At a third point in time 806, once the calibration 822 has been completed, the second part of the tracking phase 816 starts and the XR device 110 associates the calibration generated for the second user with the bending data of the second user (as mentioned above, this is done without having to identify the second user or store data that reveals the identity of the second user). This allows the XR device 110 to utilize the calibration in future, e.g., when the second user uses the XR device 110 in a subsequent user session.

At a fourth point in time 808, the second user removes the XR device 110. At a fifth point in time 810, another user switch occurs with the first user ("User A") putting the XR device 110 on again. The XR device 110 starts a new user session and detects the hands of the first user during the detection phase 818, while also checking the bending of the XR device 110. The XR device 110 determines that the bending matches the previous bending data that was obtained when the first user wore the XR device 110 and thus, at a sixth point in time 812, loads the relevant hand calibration corresponding to the bending data. The relevant hand calibration is used to initialize and run the tracking phase 820.

Figure 9:
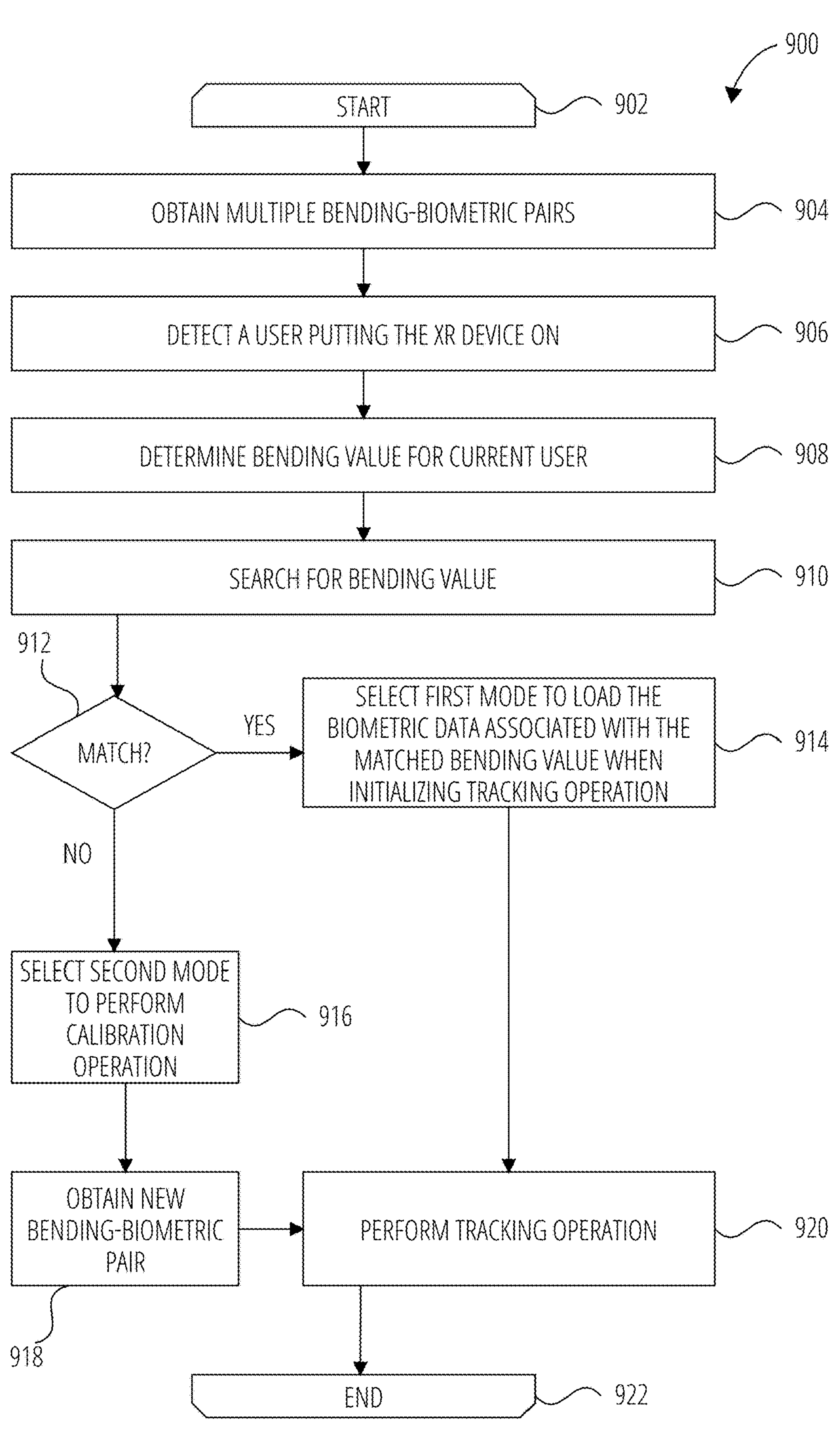
FIG. 9 is a flowchart illustrating a method suitable for analyzing bending data to determine whether to use previously identified biometric data in a tracking operation of an XR device, according to some examples.

FIG. 9 is a flowchart illustrating a method 900 suitable for analyzing bending data to determine whether to use previously identified biometric data in a tracking operation of an XR device, according to some examples. Operations in the method 900 may be performed by the XR device 110 using components (e.g., parts, modules, systems, or engines) described above with respect to FIGS. 1 and 4. Accordingly, by way of example and not limitation, the method 900 is described with reference to the XR device 110 and certain components thereof.

In the method 900, the XR device 110 is a head-wearable device, e.g., AR glasses. Further, in the method 900, the tracking operation is a hand tracking operation. However, it will be appreciated that similar techniques may be applied with respect to other types of XR devices or other types of tracking operations, e.g., the tracking of other features, such as other body parts of a user.

The method 900 commences at opening loop element 902 and proceeds to operation 904, where the XR device 110 obtains or has access to multiple "bending-biometric pairs." Each pair includes bending data (e.g., a bending value in degrees or a strain measurement) and corresponding biometric data (e.g., hand size calibration data). The XR device 110 is thus able to locate a bending value and find its corresponding biometric data, e.g., from within the cache component 442 of FIG. 4 where such data is temporarily located.

At operation 906, the XR device 110 detects that a user has put the XR device 110 on. The XR device 110 uses the bending measurement system 422 to measure or estimate the bending of the XR device 110 caused by the head of the current user, thus yielding bending data at operation 908. The XR device 110 then searches for matching bending data by checking the bending-biometric pairs at operation 910. For example, where the bending data includes a frame bending value expressed in degrees, the XR device 110 checks for the same value or a value that is within an acceptable bending range of the frame bending value.

If the XR device 110 determines, at decision operation 912, that the bending data of operation 908 matches bending data in the bending-biometric pairs, the corresponding biometric data (e.g., the associated hand feature calibration) is loaded at operation 914 as part of a first mode of the XR device 110, and the biometric data is used to initialize or run the hand tracking operation. The XR device 110 may thus determine, based on XR device bending and without having access to a user identity or user profile, that the current user matches one of the users for whom a bending-biometric pair is already available. The XR device 110 then performs hand tracking by reusing the previous hand feature calibration at operation 920.

On the other hand, if the XR device 110 determines at decision operation 912 that the bending data of the operation 908 does not match any bending data in the bending-biometric pairs, the XR device 110 performs a "fresh" calibration, e.g., hand size calibration, to obtain new biometric data with which to initialize the hand tracking operation (operation 916). The XR device 110 may thus select a second mode in which previous data is not used in response to determining (at decision operation 912) that there is no match. The new bending-biometric pair, e.g., the bending value for the current user together with the corresponding hand size calibration, can be added to the existing bending-biometric pairs (operation 918). The XR device 110 then performs hand tracking by using the new hand size calibration for the current user at operation 920. The method 900 concludes at closing loop element 922.

In some examples, the obtained bending data and biometric data may be processed to obtain a function or a rules-based engine, which takes a current bending value as an input and provides, as output, an indication or prediction of corresponding biometric data, e.g., a corresponding hand size that can be used by the XR device 110 to perform hand tracking.

In some examples, the predicted biometric data may be generated using a machine learning model. For example, the machine learning model may be trained based on classification learning by using a training data set comprising pairs of bending values with corresponding hand sizes, thereby learning to predict, for a given input bending value, an estimated hand size. As another example, the machine learning model may be trained based on clustering (unsupervised learning) to identify inherent groupings in the data, thereby learning to assign input bending data to a group or cluster (e.g., range) of hand sizes. The processor 404 of the XR device 110 may execute or implement a prediction component, e.g., as part of the calibration system 420 or the bending measurement system 422, which outputs predicted biometric data as referred to above. The prediction component may run a rules-based engine or execute a machine learning model as referred to above. It is noted that any training data used in such machine learning approaches, or data used to implement a rules-based engine, contains only anonymized data, e.g., only bending values with corresponding hand sizes, without any information that can reveal the identity of a user or a user profile.

In some examples, determining whether to use previously identified biometric data in a tracking operation may thus include providing bending data as input to a processor-implemented prediction component to obtain predicted biometric data, and comparing the predicted biometric data with previously identified biometric data. For example, if the predicted biometric data matches previously identified biometric data, the XR device 110 may use the previously identified biometric data instead of running a "fresh" calibration operation.

Figure 10:
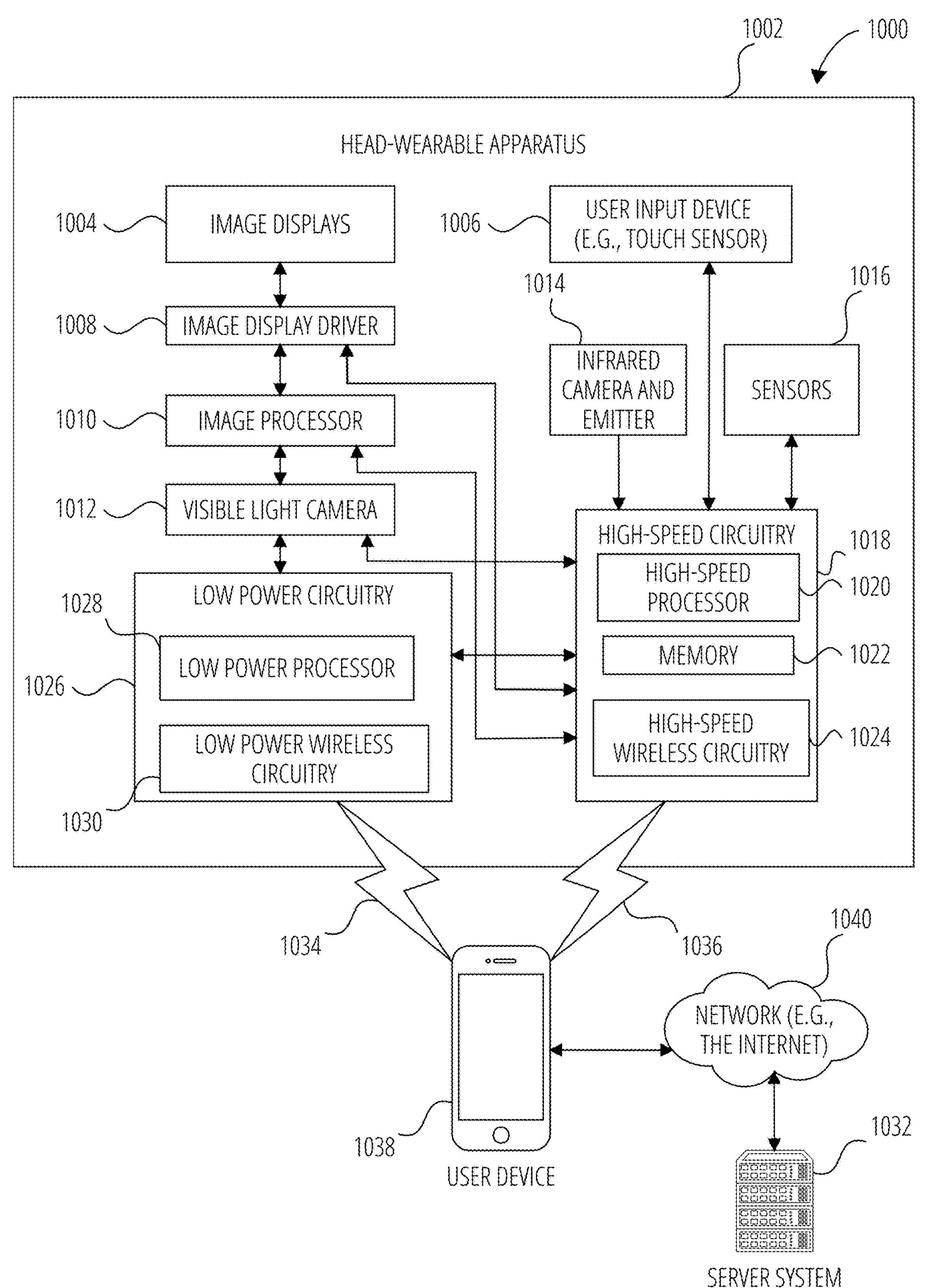
FIG. 10 illustrates a network environment in which a head-wearable apparatus can be implemented according to some examples.

FIG. 10 illustrates a network environment 1000 in which a head-wearable apparatus 1002, e.g., a head-wearable XR device, can be implemented according to some examples. FIG. 10 provides a high-level functional block diagram of an example head-wearable apparatus 1002 communicatively coupled to a mobile user device 1038 and a server system 1032 via a suitable network 1040. One or more of the techniques described herein may be performed using the head-wearable apparatus 1002 or a network of devices similar to those shown in FIG. 10. The head-wearable apparatus 1002 may be a flexible device.

The head-wearable apparatus 1002 includes a camera, such as at least one of a visible light camera 1012 and an infrared camera and emitter 1014. The head-wearable apparatus 1002 includes other sensors 1016, such as motion sensors or eye tracking sensors. The user device 1038 can be capable of connecting with head-wearable apparatus 1002 using both a communication link 1034 and a communication link 1036. The user device 1038 is connected to the server system 1032 via the network 1040. The network 1040 may include any combination of wired and wireless connections.

The head-wearable apparatus 1002 includes a display arrangement that has several components. The arrangement includes two image displays 1004 of an optical assembly. The two displays include one associated with the left lateral side and one associated with the right lateral side of the head-wearable apparatus 1002. The head-wearable apparatus 1002 also includes an image display driver 1008, an image processor 1010, low power circuitry 1026, and high-speed circuitry 1018. The image displays 1004 are for presenting images and videos, including an image that can provide a graphical user interface to a user of the head-wearable apparatus 1002.

The image display driver 1008 commands and controls the image display of each of the image displays 1004. The image display driver 1008 may deliver image data directly to each image display of the image displays 1004 for presentation or may have to convert the image data into a signal or data format suitable for delivery to each image display device. For example, the image data may be video data formatted according to compression formats, such as H. 264 (MPEG-4 Part 10), HEVC, Theora, Dirac, RealVideo RV40, VP8, VP9, or the like, and still image data may be formatted according to compression formats such as Portable Network Group (PNG), Joint Photographic Experts Group (JPEG), Tagged Image File Format (TIFF) or exchangeable image file format (Exif) or the like.

The head-wearable apparatus 1002 may include a frame and stems (or temples) extending from a lateral side of the frame, or another component to facilitate wearing of the head-wearable apparatus 1002 by a user. The head-wearable apparatus 1002 of FIG. 10 further includes a user input device 1006 (e.g., touch sensor or push button) including an input surface on the head-wearable apparatus 1002. The user input device 1006 is configured to receive, from the user, an input selection to manipulate the graphical user interface of the presented image.

The components shown in FIG. 10 for the head-wearable apparatus 1002 are located on one or more circuit boards, for example a printed circuit board (PCB) or flexible PCB, in the rims or temples. Alternatively, or additionally, the depicted components can be located in the chunks, frames, hinges, or bridges of the head-wearable apparatus 1002. Left and right sides of the head-wearable apparatus 1002 can each include a digital camera element such as a complementary metal-oxide-semiconductor (CMOS) image sensor, charge coupled device, a camera lens, or any other respective visible or light capturing elements that may be used to capture data, including images of scenes with unknown objects.

The head-wearable apparatus 1002 includes a memory 1022 which stores instructions to perform a subset or all of the functions described herein. The memory 1022 can also include a storage device. As further shown in FIG. 10, the high-speed circuitry 1018 includes a high-speed processor 1020, the memory 1022, and high-speed wireless circuitry 1024. In FIG. 10, the image display driver 1008 is coupled to the high-speed circuitry 1018 and operated by the high-speed processor 1020 in order to drive the left and right image displays of the image displays 1004. The high-speed processor 1020 may be any processor capable of managing high-speed communications and operation of any general computing system needed for the head-wearable apparatus 1002. The high-speed processor 1020 includes processing resources needed for managing high-speed data transfers over the communication link 1036 to a wireless local area network (WLAN) using high-speed wireless circuitry 1024. In certain examples, the high-speed processor 1020 executes an operating system such as a LINUX operating system or other such operating system of the head-wearable apparatus 1002 and the operating system is stored in memory 1022 for execution. In addition to any other responsibilities, the high-speed processor 1020 executing a software architecture for the head-wearable apparatus 1002 is used to manage data transfers with high-speed wireless circuitry 1024. In certain examples, high-speed wireless circuitry 1024 is configured to implement Institute of Electrical and Electronic Engineers (IEEE) 1002.11 communication standards, also referred to herein as Wi-Fi™. In other examples, other high-speed communications standards may be implemented by high-speed wireless circuitry 1024.

The low power wireless circuitry 1030 and the high-speed wireless circuitry 1024 of the head-wearable apparatus 1002 can include short range transceivers (Bluetooth™) and wireless wide, local, or wide area network transceivers (e.g., cellular or Wi-Fi™). The user device 1038, including the transceivers communicating via the communication link 1034 and communication link 1036, may be implemented using details of the architecture of the head-wearable apparatus 1002, as can other elements of the network 1040.

The memory 1022 may include a storage device capable of storing various data and applications, including, among other things, camera data generated by the visible light camera 1012, sensors 1016, and the image processor 1010, as well as images generated for display by the image display driver 1008 on the image displays of the image displays 1004. While the memory 1022 is shown as integrated with the high-speed circuitry 1018, in other examples, the memory 1022 may be an independent standalone element of the head-wearable apparatus 1002. In certain such examples, electrical routing lines may provide a connection through a chip that includes the high-speed processor 1020 from the image processor 1010 or low power processor 1028 to the memory 1022. In other examples, the high-speed processor 1020 may manage addressing of memory 1022 such that the low power processor 1028 will boot the high-speed processor 1020 any time that a read or write operation involving memory 1022 is needed.

As shown in FIG. 10, the low power processor 1028 or high-speed processor 1020 of the head-wearable apparatus 1002 can be coupled to the camera (visible light camera 1012, or infrared camera and emitter 1014), the image display driver 1008, the user input device 1006 (e.g., touch sensor or push button), and the memory 1022. The head-wearable apparatus 1002 also includes sensors 1016, which may be the motion components 1434, position components 1438, environmental components 1436, and biometric components 1432, e.g., as described below with reference to FIG. 14. In particular, motion components 1434 and position components 1438 are used by the head-wearable apparatus 1002 to determine and keep track of the position and orientation (the "pose") of the head-wearable apparatus 1002 relative to a frame of reference or another object, in conjunction with a video feed from one of the visible light cameras 1012, using for example techniques such as structure from motion (SfM) or VIO.

In some examples, and as shown in FIG. 10, the head-wearable apparatus 1002 is connected with a host computer. For example, the head-wearable apparatus 1002 is paired with the user device 1038 via the communication link 1036 or connected to the server system 1032 via the network 1040. The server system 1032 may be one or more computing devices as part of a service or network computing system, for example, that include a processor, a memory, and network communication interface to communicate over the network 1040 with the user device 1038 and head-wearable apparatus 1002.

The user device 1038 includes a processor and a network communication interface coupled to the processor. The network communication interface allows for communication over the network 1040, communication link 1034 or communication link 1036. The user device 1038 can further store at least portions of the instructions for implementing functionality described herein.

Output components of the head-wearable apparatus 1002 include visual components, such as a display (e.g., one or more liquid-crystal display (LCD)), one or more plasma display panel (PDP), one or more light emitting diode (LED) display, one or more projector, or one or more waveguide. The image displays 1004 of the optical assembly are driven by the image display driver 1008. The output components of the head-wearable apparatus 1002 further include acoustic components (e.g., speakers), haptic components (e.g., a vibratory motor), other signal generators, and so forth. The input components of the head-wearable apparatus 1002, the user device 1038, and server system 1032, such as the user input device 1006, may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

The head-wearable apparatus 1002 may optionally include additional peripheral device elements. Such peripheral device elements may include biometric sensors, additional sensors, or display elements integrated with the head-wearable apparatus 1002. For example, peripheral device elements may include any I/O components including output components, motion components, position components, or any other such elements described herein.

For example, the biometric components include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components include acceleration sensor components (e.g., accelerometer), gravitation sensor components, rotation sensor components (e.g., gyroscope), and so forth. The position components include location sensor components to generate location coordinates (e.g., a Global Positioning System (GPS) receiver component), Wi-Fi™ or Bluetooth™ transceivers to generate positioning system coordinates, altitude sensor components (e.g., altimeters or barometers that detect air pressure from which altitude may be derived), orientation sensor components (e.g., magnetometers), and the like. Such positioning system coordinates can also be received over a communication link 1036 from the user device 1038 via the low power wireless circuitry 1030 or high-speed wireless circuitry 1024.

As confirmed elsewhere herein, any biometric data collected by biometric components is captured and stored only with user approval and deleted on user request. Further, biometric data referred to herein may be used for very limited purposes and not stored persistently. To ensure limited and authorized use of biometric information and other personally identifiable information (PII), access to this data is restricted to authorized personnel only, if at all. Any use of biometric data may strictly be limited to specific purposes, such as for use in hand tracking, and such data is not shared or sold to any third party without the explicit consent of the user. In addition, appropriate technical and organizational measures are implemented to ensure the security and confidentiality of this sensitive information.

Figure 11:
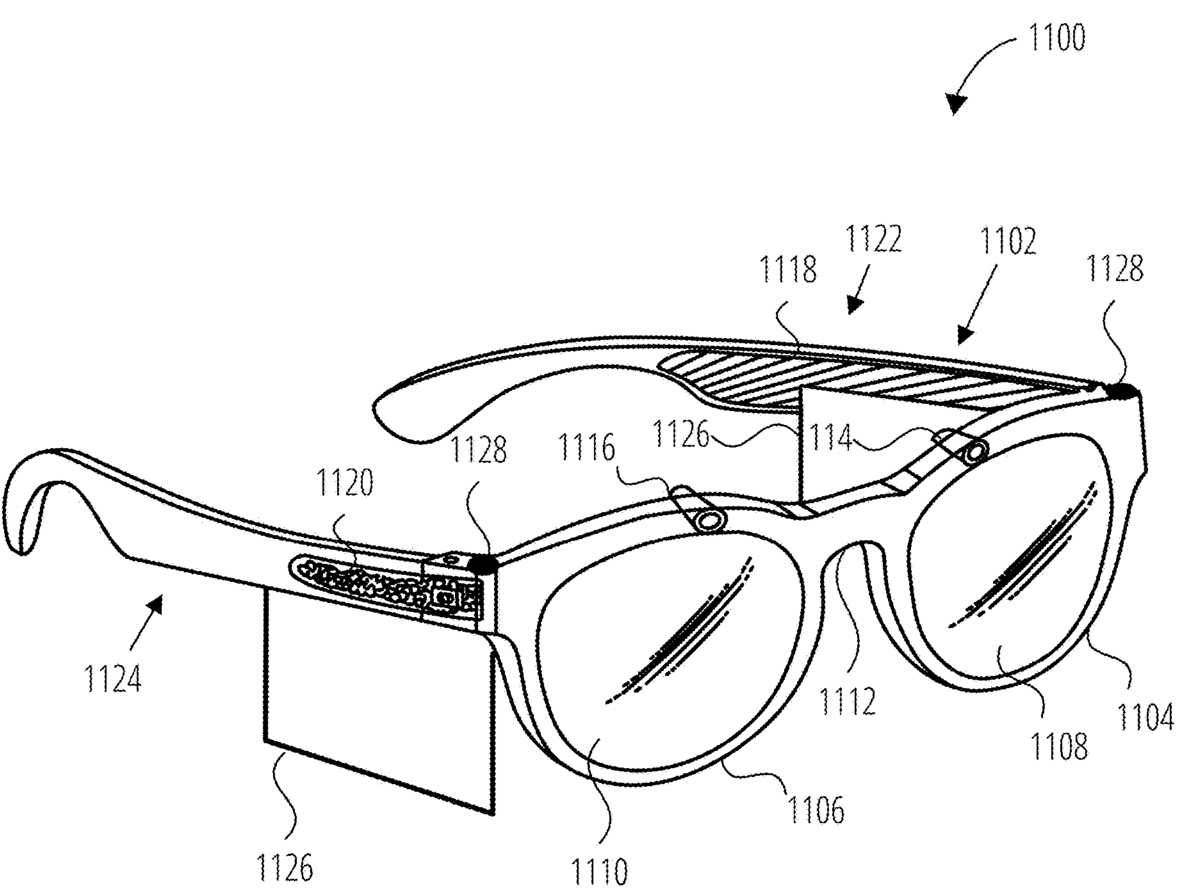
FIG. 11 is a perspective view of a head-worn device, in accordance with some examples.

FIG. 11 is a perspective view of a head-worn XR device (e.g., glasses 1100), in accordance with some examples. The glasses 1100 can include a frame 1102 made from any suitable material such as plastic or metal, including any suitable shape memory alloy. In some examples, the glasses 1100 is a flexible device as defined herein.

In one or more examples, the frame 1102 includes a first or left optical element holder 1104 (e.g., a display or lens holder) and a second or right optical element holder 1106 connected by a bridge 1112. A first or left optical element 1108 and a second or right optical element 1110 can be provided within respective left optical element holder 1104 and right optical element holder 1106. The right optical element 1110 and the left optical element 1108 can be a lens, a display, a display assembly, or a combination of the foregoing. Any suitable display assembly can be provided in the glasses 1100.

The frame 1102 additionally includes a left arm or temple piece 1122 and a right arm or temple piece 1124. In some examples the frame 1102 can be formed from a single piece of material so as to have a unitary or integral construction.

The glasses 1100 can include a computing device, such as a computer 1120, which can be of any suitable type so as to be carried by the frame 1102 and, in one or more examples, of a suitable size and shape, so as to be partially disposed in one of the temple piece 1122 or the temple piece 1124. The computer 1120 can include one or more processors with memory, wireless communication circuitry, and a power source. As discussed with reference to FIG. 10, the computer 1120 may comprise low-power circuitry, high-speed circuitry, and a display processor. Various other examples may include these elements in different configurations or integrated together in different ways.

The computer 1120 additionally includes a battery 1118 or other suitable portable power supply. In some examples, the battery 1118 is disposed in left temple piece 1122 and is electrically coupled to the computer 1120 disposed in the right temple piece 1124. The glasses 1100 can include a connector or port (not shown) suitable for charging the battery 1118, a wireless receiver, transmitter or transceiver (not shown), or a combination of such devices.

The glasses 1100 include a first or left camera 1114 and a second or right camera 1116. Although two cameras are depicted, other examples contemplate the use of a single or additional (i.e., more than two) cameras. In one or more examples, the glasses 1100 include any number of input sensors or other input/output devices in addition to the left camera 1114 and the right camera 1116. Such sensors or input/output devices can additionally include biometric sensors, location sensors, motion sensors, bending sensors, and so forth.

In some examples, the left camera 1114 and the right camera 1116 provide video frame data for use by the glasses 1100 to extract 3D information from a real world scene.

The glasses 1100 may also include a touchpad 1126 mounted to or integrated with one or both of the left temple piece 1122 and right temple piece 1124. The touchpad 1126 is generally vertically-arranged, approximately parallel to a user's temple in some examples. As used herein, generally vertically aligned means that the touchpad is more vertical than horizontal, although potentially more vertical than that. Additional user input may be provided by one or more buttons 1128, which in the illustrated examples are provided on the outer upper edges of the left optical element holder 1104 and right optical element holder 1106. The one or more touchpads 1126 and buttons 1128 provide a means whereby the glasses 1100 can receive input from a user of the glasses 1100.

Figure 12:
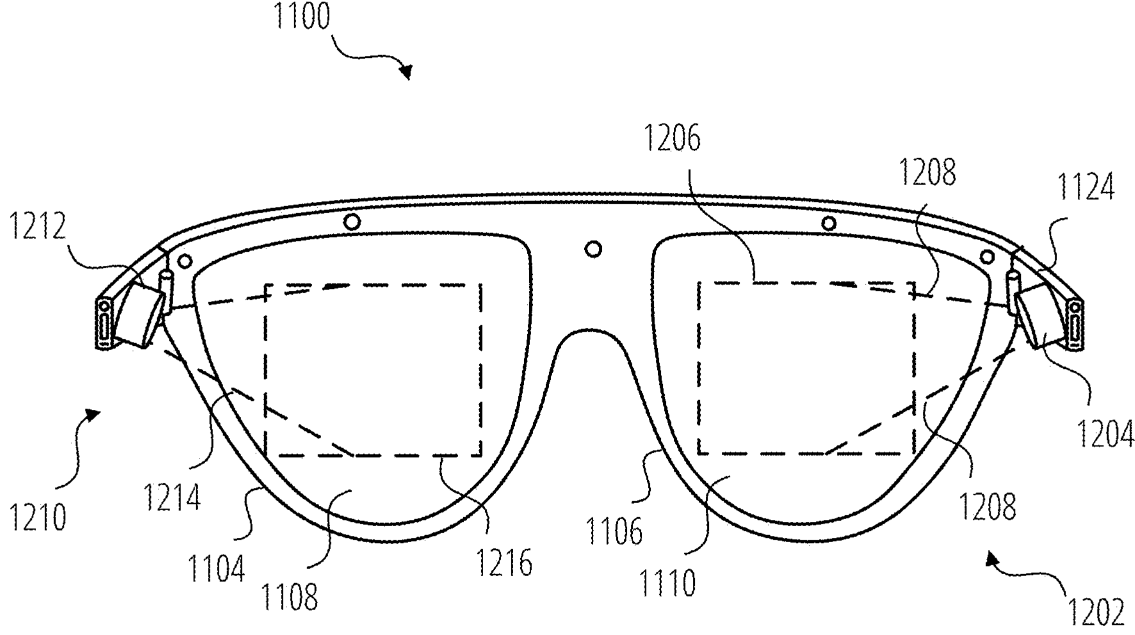
FIG. 12 illustrates a further view of the head-worn device of FIG. 11, in accordance with some examples.

FIG. 12 illustrates the glasses 1100 from the perspective of a user. For clarity, a number of the elements shown in FIG. 11 have been omitted. As described in FIG. 11, the glasses 1100 shown in FIG. 12 include left optical element 1108 and right optical element 1110 secured within the left optical element holder 1104 and the right optical element holder 1106 respectively.

The glasses 1100 include forward optical assembly 1202 comprising a right projector 1204 and a right near eye display 1206, and a forward optical assembly 1210 including a left projector 1212 and a left near eye display 1216.

In some examples, the near eye displays are waveguides. The waveguides include reflective or diffractive structures (e.g., gratings and/or optical elements such as mirrors, lenses, or prisms). Light 1208 emitted by the projector 1204 encounters the diffractive structures of the waveguide of the near eye display 1206, which directs the light towards the right eye of a user to provide an image on or in the right optical element 1110 that overlays the view of the real world seen by the user. Similarly, light 1214 emitted by the projector 1212 encounters the diffractive structures of the waveguide of the near eye display 1216, which directs the light towards the left eye of a user to provide an image on or in the left optical element 1108 that overlays the view of the real world seen by the user. The combination of a GPU, the forward optical assembly 1202, the left optical element 1108, and the right optical element 1110 provide an optical engine of the glasses 1100. The glasses 1100 use the optical engine to generate an overlay of the real world view of the user including display of a 3D user interface to the user of the glasses 1100.

It will be appreciated however that other display technologies or configurations may be utilized within an optical engine to display an image to a user in the user's field of view. For example, instead of a projector 1204 and a waveguide, an LCD, LED or other display panel or surface may be provided.

In use, a user of the glasses 1100 will be presented with information, content and various 3D user interfaces on the near eye displays. As described in more detail herein, the user can then interact with the glasses 1100 using a touchpad 1126 and/or the buttons 1128, voice inputs or touch inputs on an associated device, and/or hand movements, locations, and positions detected by the glasses 1100.

Figure 13:
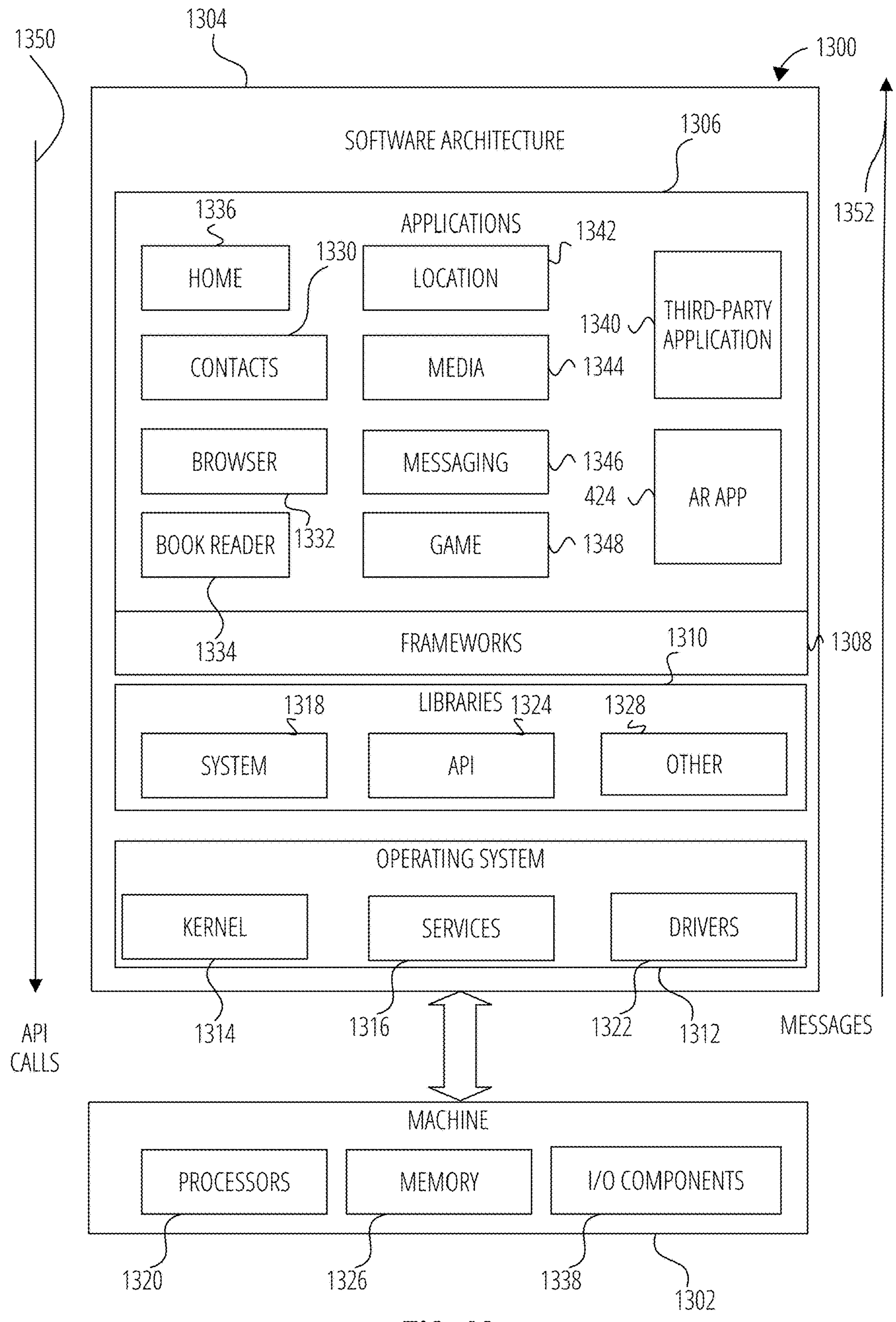
FIG. 13 is a block diagram showing a software architecture within which the present disclosure may be implemented, according to some examples.

FIG. 13 is a block diagram 1300 illustrating a software architecture 1304, which can be installed on any one or more of the devices described herein. The software architecture 1304 is supported by hardware such as a machine 1302 that includes processors 1320, memory 1326, and I/O components 1338. In this example, the software architecture 1304 can be conceptualized as a stack of layers, where each layer provides a particular functionality. The software architecture 1304 includes layers such as an operating system 1312, libraries 1310, frameworks 1308, and applications 1306. Operationally, the applications 1306 invoke Application Programming Interface calls or API calls 1350, through the software stack and receive messages 1352 in response to the API calls 1350.

The operating system 1312 manages hardware resources and provides common services. The operating system 1312 includes, for example, a kernel 1314, services 1316, and drivers 1322. The kernel 1314 acts as an abstraction layer between the hardware and the other software layers. For example, the kernel 1314 provides memory management, processor management (e.g., scheduling), component management, networking, and security settings, among other functionality. The services 1316 can provide other common services for the other software layers. The drivers 1322 are responsible for controlling or interfacing with the underlying hardware. For instance, the drivers 1322 can include display drivers, camera drivers, Bluetooth™ or Bluetooth™ Low Energy drivers, flash memory drivers, serial communication drivers (e.g., Universal Serial Bus (USB) drivers), WI-FI™ drivers, audio drivers, power management drivers, and so forth.

The libraries 1310 provide a low-level common infrastructure used by the applications 1306. The libraries 1310 can include system libraries 1318 (e.g., C standard library) that provide functions such as memory allocation functions, string manipulation functions, mathematic functions, and the like. In addition, the libraries 1310 can include API libraries 1324 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1310 can also include a wide variety of other libraries 1328 to provide many other APIs to the applications 1306.

The frameworks 1308 provide a high-level common infrastructure that is used by the applications 1306. For example, the frameworks 1308 provide various graphical user interface (GUI) functions, high-level resource management, and high-level location services. The frameworks 1308 can provide a broad spectrum of other APIs that can be used by the applications 1306, some of which may be specific to a particular operating system or platform.

In some examples, the applications 1306 may include a home application 1336, a contacts application 1330, a browser application 1332, a book reader application 1334, a location application 1342, a media application 1344, a messaging application 1346, a game application 1348, and a broad assortment of other applications such as a third-party application 1340. The applications 1306 are programs that execute functions defined in the programs. Various programming languages can be employed to create one or more of the applications 1306, structured in a variety of manners, such as object-oriented programming languages (e.g., Objective-C, Java, or C++) or procedural programming languages (e.g., C or assembly language). In some examples, the third-party application 1340 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In FIG. 13, the third-party application 1340 can invoke the API calls 1350 provided by the operating system 1312 to facilitate functionality described herein. The applications 1306 may include an AR application such as the AR application 424 described herein, according to some examples.

Figure 14:
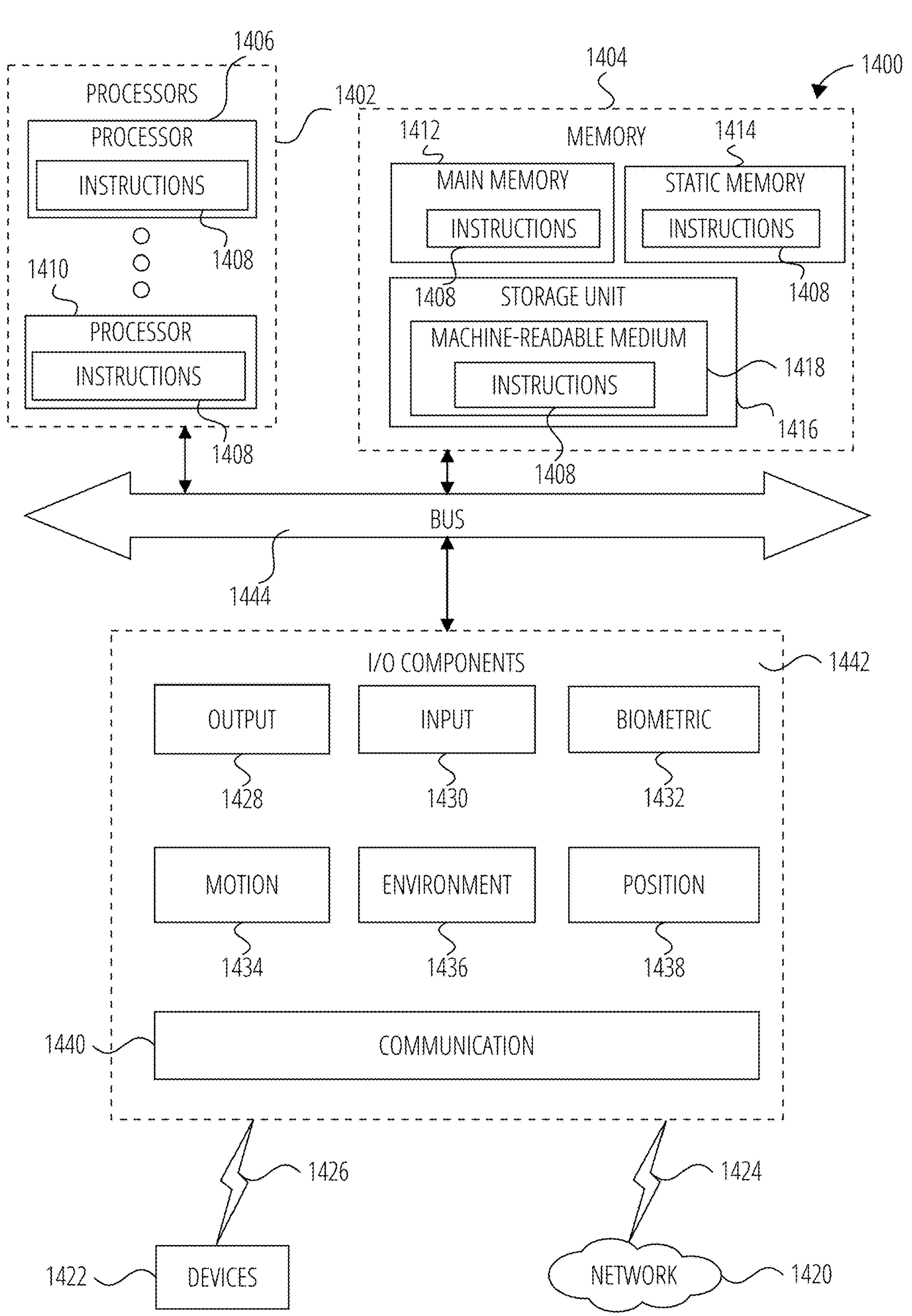
FIG. 14 is a diagrammatic representation of a machine in the form of a computer system within which a set of instructions may be executed for causing the machine to perform any one or more of the methodologies discussed herein, according to some examples.

FIG. 14 is a diagrammatic representation of a machine 1400 within which instructions 1408 (e.g., software, a program, an application, an applet, an app, or other executable code) for causing the machine 1400 to perform any one or more of the methodologies discussed herein may be executed. For example, the instructions 1408 may cause the machine 1400 to execute any one or more of the methods described herein. The instructions 1408 transform the general, non-programmed machine 1400 into a particular machine 1400 programmed to carry out the described and illustrated functions in the manner described. The machine 1400 may operate as a standalone device or may be coupled (e.g., networked) to other machines. In a networked deployment, the machine 1400 may operate in the capacity of a server machine or a client machine in a server-client network environment, or as a peer machine in a peer-to-peer (or distributed) network environment. The machine 1400 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), XR device (e.g., flexible device), AR device, VR device, a smart home device (e.g., a smart appliance), other smart devices, a web appliance, a network router, a network switch, a network bridge, or any machine capable of executing the instructions 1408, sequentially or otherwise, that specify actions to be taken by the machine 1400. Further, while only a single machine 1400 is illustrated, the term "machine" shall also be taken to include a collection of machines that individually or jointly execute the instructions 1408 to perform any one or more of the methodologies discussed herein.

The machine 1400 may include processors 1402, memory 1404, and I/O components 1442, which may be configured to communicate with each other via a bus 1444. In some examples, the processors 1402 (e.g., a Central Processing Unit (CPU), a Reduced Instruction Set Computing (RISC) processor, a Complex Instruction Set Computing (CISC) Processor, a Graphics Processing Unit (GPU), a Digital Signal Processor (DSP), an ASIC, a Radio-Frequency Integrated Circuit (RFIC), another processor, or any suitable combination thereof) may include, for example, a processor 1406 and a processor 1410 that execute the instructions 1408. The term "processor" is intended to include multi-core processors that may comprise two or more independent processors (sometimes referred to as "cores") that may execute instructions contemporaneously. Although FIG. 14 shows multiple processors 1402, the machine 1400 may include a single processor with a single core, a single processor with multiple cores (e.g., a multi-core processor), multiple processors with a single core, multiple processors with multiples cores, or any combination thereof.

The memory 1404 includes a main memory 1412, a static memory 1414, and a storage unit 1416, accessible to the processors via the bus 1444. The main memory 1404, the static memory 1414, and storage unit 1416 store the instructions 1408 embodying any one or more of the methodologies or functions described herein. The instructions 1408 may also reside, completely or partially, within the main memory 1412, within the static memory 1414, within machine-readable medium 1418 within the storage unit 1416, within at least one of the processors, or any suitable combination thereof, during execution thereof by the machine 1400.

The I/O components 1442 may include a wide variety of components to receive input, provide output, produce output, transmit information, exchange information, capture measurements, and so on. The specific I/O components 1442 that are included in a particular machine will depend on the type of machine. For example, portable machines such as mobile phones may include a touch input device or other such input mechanisms, while a headless server machine will likely not include such a touch input device. It will be appreciated that the I/O components 1442 may include many other components that are not shown in FIG. 14. In various examples, the I/O components 1442 may include output components 1428 and input components 1430. The output components 1428 may include visual components (e.g., a display such as a plasma display panel (PDP), a light emitting diode (LED) display, a LCD, a projector, or a cathode ray tube (CRT)), acoustic components (e.g., speakers), haptic components (e.g., a vibratory motor, resistance mechanisms), other signal generators, and so forth. The input components 1430 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In some examples, the I/O components 1442 may include biometric components 1432, motion components 1434, environmental components 1436, or position components 1438, among a wide array of other components. For example, the biometric components 1432 include components to detect expressions (e.g., hand expressions, facial expressions, vocal expressions, body gestures, or eye tracking), measure biosignals (e.g., blood pressure, heart rate, body temperature, perspiration, or brain waves), detect features of the hand of a user, identify a person (e.g., voice identification, retinal identification, facial identification, fingerprint identification, or electroencephalogram-based identification), and the like. The motion components 1434 include acceleration sensor components (e.g., accelerometer), gravitation sensor components, rotation sensor components (e.g., gyroscope), and so forth. The environmental components 1436 include, for example, illumination sensor components (e.g., photometer), temperature sensor components (e.g., one or more thermometers that detect ambient temperature), humidity sensor components, pressure sensor components (e.g., barometer), bending sensor components (e.g., strain gauge used to assess frame bending) acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1438 include location sensor components (e.g., a GPS receiver components), altitude sensor components (e.g., altimeters or barometers that detect air pressure from which altitude may be derived), orientation sensor components (e.g., magnetometers), and the like.

As confirmed elsewhere herein, any biometric data collected by biometric components is captured and stored only with user approval and deleted on user request. Further, biometric data referred to herein may be used for very limited purposes and not stored persistently. To ensure limited and authorized use of biometric information and other personally identifiable information (PII), access to this data is restricted to authorized personnel only, if at all. Any use of biometric data may strictly be limited to specific purposes, such as for use in hand tracking, and such data is not shared or sold to any third party without the explicit consent of the user. In addition, appropriate technical and organizational measures are implemented to ensure the security and confidentiality of this sensitive information.

Communication may be implemented using a wide variety of technologies. The I/O components 1442 further include communication components 1440 operable to couple the machine 1400 to a network 1420 or devices 1422 via a coupling 1424 and a coupling 1426, respectively. For example, the communication components 1440 may include a network interface component or another suitable device to interface with the network 1420. In further examples, the communication components 1440 may include wired communication components, wireless communication components, cellular communication components, Near Field Communication (NFC) components, Bluetooth™ components, Wi-Fi™ components, and other communication components to provide communication via other modalities. The devices 1422 may include another machine or any of a wide variety of peripheral devices (e.g., a peripheral device coupled via a USB).

Moreover, the communication components 1440 may detect identifiers or include components operable to detect identifiers. For example, the communication components 1440 may include Radio Frequency Identification (RFID) tag reader components, NFC smart tag detection components, optical reader components (e.g., an image sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1440, such as location via Internet Protocol (IP) geolocation, location via Wi-Fi™ signal triangulation, location via detecting an NFC beacon signal that may indicate a particular location, and so forth.

The various memories (e.g., memory 1404, main memory 1412, static memory 1414, and/or memory of the processors 1402) and/or storage unit 1416 may store one or more sets of instructions and data structures (e.g., software) embodying or used by any one or more of the methodologies or functions described herein. These instructions (e.g., the instructions 1408), when executed by processors 1402, cause various operations to implement the disclosed examples.

The instructions 1408 may be transmitted or received over the network 1420, using a transmission medium, via a network interface device (e.g., a network interface component included in the communication components 1440) and using any one of a number of well-known transfer protocols (e.g., hypertext transfer protocol (HTTP)). Similarly, the instructions 1408 may be transmitted or received using a transmission medium via the coupling 1426 (e.g., a peer-to-peer coupling) to the devices 1422.

As used herein, the terms "machine-storage medium," "device-storage medium," and "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media, and/or device-storage media include non-volatile memory, including by way of example semiconductor memory devices, e.g., erasable programmable read-only memory (EPROM), electrically erasable programmable read-only memory (EEPROM), field-programmable gate arrays (FPGAs), and flash memory devices; magnetic disks such as internal hard disks and removable disks; magneto-optical disks; and CD-ROM and DVD-ROM disks.

The terms "transmission medium" and "signal medium" mean the same thing and may be used interchangeably in this disclosure. The terms "transmission medium" and "signal medium" shall be taken to include any intangible medium that is capable of storing, encoding, or carrying the instructions for execution by the machine 1400, and include digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a manner as to encode information in the signal.

CONCLUSION

Although aspects have been described with reference to specific examples, it will be evident that various modifications and changes may be made to these examples without departing from the broader scope of the present disclosure. Accordingly, the specification and drawings are to be regarded in an illustrative rather than a restrictive sense. The accompanying drawings that form a part hereof, show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This Detailed Description, therefore, is not to be taken in a limiting sense, and the scope of various examples is defined only by the appended claims, along with the full range of equivalents to which such claims are entitled.

As used in this disclosure, phrases of the form "at least one of an A, a B, or a C," "at least one of A, B, or C," "at least one of A, B, and C," and the like, should be interpreted to select at least one from the group that comprises "A, B, and C." Unless explicitly stated otherwise in connection with a particular instance in this disclosure, this manner of phrasing does not mean "at least one of A, at least one of B, and at least one of C." As used in this disclosure, the example "at least one of an A, a B, or a C," would cover any of the following selections: {A}, {B}, {C}, {A, B}, {A, C}, {B, C}, and {A, B, C}.

Unless the context clearly requires otherwise, throughout the description and the claims, the words "comprise," "comprising," and the like are to be construed in an inclusive sense, as opposed to an exclusive or exhaustive sense, e.g., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise, the term "and/or" in reference to a list of two or more items, covers all of the following interpretations of the word: any one of the items in the list, all of the items in the list, and any combination of the items in the list.

The various features, steps, operations, and processes described herein may be used independently of one another, or may be combined in various ways. All possible combinations and subcombinations are intended to fall within the scope of this disclosure. In addition, certain method or process blocks or operations may be omitted in some implementations.

Although some examples, e.g., those depicted in the drawings, include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in examples for the purpose of streamlining the disclosure. This method of disclosure is not to be interpreted as reflecting an intention that the examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

EXAMPLES

In view of the above-described implementations of subject matter this application discloses the following list of examples, wherein one feature of an example in isolation, or more than one feature of an example taken in combination, and, optionally, in combination with one or more features of one or more further examples, are further examples also falling within the disclosure of this application.

Example 1 is a method comprising: obtaining bending data indicative of bending of an extended reality (XR) device to accommodate a body part of a user wearing the XR device; determining, based on the bending data, whether to use previously identified biometric data in a tracking operation; responsive to determining whether to use the previously identified biometric data, selecting a mode of the XR device, the selected mode being a first mode or a second mode, the first mode being based on determining to use the previously identified biometric data in the tracking operation and the second mode being based on determining not to use the previously identified biometric data in the tracking operation; and using the selected mode to initialize the tracking operation.

In Example 2, the subject matter of Example 1 includes, wherein the tracking operation comprises tracking a feature of the user wearing the XR device.

In Example 3, the subject matter of Example 2 includes, wherein the feature is a hand of the user wearing the XR device, and the previously identified biometric data comprises a previously obtained hand feature calibration.

In Example 4, the subject matter of any of Examples 1-3 includes, wherein the previously identified biometric data comprises a hand feature estimate generated during a previous user session.

In Example 5, the subject matter of any of Examples 1-4 includes, wherein the bending data comprises at least one of: a measurement of the bending of the XR device generated by at least one sensor of the XR device; or an estimate of the bending of the XR device.

In Example 6, the subject matter of any of Examples 1-5 includes, wherein the bending data is first bending data, and wherein the determining whether to use the previously identified biometric data in the tracking operation comprises: comparing the first bending data to second bending data associated with the previously identified biometric data.

In Example 7, the subject matter of Example 6 includes, wherein the second bending data comprises a measurement or estimate of the bending of the XR device generated during a previous user session.

In Example 8, the subject matter of any of Examples 6-7 includes, wherein the selected mode is the first mode in which the previously identified biometric data is selected for use in the initializing of the tracking operation, and the first mode is selected based on determining that the first bending data matches the second bending data.

In Example 9, the subject matter of Example 8 includes, identifying, based on the determining that the first bending data matches the second bending data, that no calibration operation is required for the user.

In Example 10, the subject matter of Example 9 includes, adjusting the previously identified biometric data during the tracking operation.

In Example 11, the subject matter of Example 10 includes, wherein the previously identified biometric data is adjusted so as to refine the biometric data across multiple user sessions.

In Example 12, the subject matter of any of Examples 8-11 includes, wherein the determining that the first bending data matches the second bending data comprises determining that the first bending data is within an acceptable bending range of the second bending data.

In Example 13, the subject matter of any of Examples 8-12 includes, detecting, based on the determining that the first bending data matches the second bending data, that the user corresponds to a previous user of the XR device, the previous user being associated with the second bending data and the previously identified biometric data.

In Example 14, the subject matter of any of Examples 6-13 includes, wherein the selected mode is the second mode in which a calibration operation is performed for the user, and the second mode is selected based on determining that the first bending data does not match the second bending data.

In Example 15, the subject matter of Example 14 includes, performing the calibration operation to obtain new biometric data for use in the tracking operation; and associating the new biometric data with the first bending data.

In Example 16, the subject matter of any of Examples 14-15 includes, detecting, based on the determining that the first bending data does not match the second bending data, that the user does not correspond to a previous user of the XR device, the previous user being associated with the second bending data and the previously identified biometric data.

Example 17 is a system comprising: at least one processor; and at least one memory component storing instructions that, when executed by the at least one processor, configure the system to perform operations comprising: obtaining bending data indicative of bending of an extended reality (XR) device to accommodate a body part of a user wearing the XR device; determining, based on the bending data, whether to use previously identified biometric data in a tracking operation; responsive to determining whether to use the previously identified biometric data, selecting a mode of the XR device, the selected mode being a first mode or a second mode, the first mode being based on determining to use the previously identified biometric data in the tracking operation and the second mode being based on determining not to use the previously identified biometric data in the tracking operation; and using the selected mode to initialize the tracking operation.

In Example 18, the subject matter of Example 17 includes, wherein the tracking operation comprises tracking a feature of the user wearing the XR device.

In Example 19, the subject matter of Example 18 includes, wherein the feature is a hand of the user wearing the XR device, and the previously identified biometric data comprises a previously obtained hand feature calibration.

Example 20 is a non-transitory computer-readable storage medium, the computer-readable storage medium including instructions that when executed by at least one processor, cause the at least one processor to perform operations comprising: obtaining bending data indicative of bending of an extended reality (XR) device to accommodate a body part of a user wearing the XR device; determining, based on the bending data, whether to use previously identified biometric data in a tracking operation; responsive to determining whether to use the previously identified biometric data, selecting a mode of the XR device, the selected mode being a first mode or a second mode, the first mode being based on determining to use the previously identified biometric data in the tracking operation and the second mode being based on determining not to use the previously identified biometric data in the tracking operation; and using the selected mode to initialize the tracking operation.

Example 21 is at least one machine-readable medium including instructions that, when executed by processing circuitry, cause the processing circuitry to perform operations to implement any of Examples 1-20.

Example 22 is an apparatus comprising means to implement any of Examples 1-20.

Example 23 is a system to implement any of Examples 1-20.

Example 24 is a method to implement any of Examples 1-20.

What is claimed is:

1. A method comprising:

obtaining bending data indicative of bending of an extended reality (XR) device to accommodate a body part of a user wearing the XR device;

determining, based on the bending data, whether to use previously identified biometric data in a tracking operation of the XR device;

selecting a mode of the XR device, the selected mode being a first mode in which the previously identified biometric data is applied in the tracking operation or a second mode in which previous biometric data is not applied in the tracking operation; and performing, by the XR device, the tracking operation based on the selected mode.

2. The method of claim 1, wherein the previously identified biometric data comprises a hand feature estimate generated during a previous user session.

3. The method of claim 1, wherein obtaining the bending data comprises:

analyzing images from a plurality of cameras of the XR device having overlapping fields of view to estimate the bending of the XR device.

4. The method of claim 3, wherein analyzing the images comprises:

generating a depth map based on matched features between views from the plurality of cameras; and analyzing the depth map to estimate the bending of the XR device.

5. The method of claim 1, wherein performing the tracking operation comprises:

implementing a detection phase identifying an object of interest; and implementing a tracking phase estimating a pose of the object over time.

6. The method of claim 5, wherein the detection phase comprises:

detecting the object of interest in a camera field of view;

detecting landmarks on the object of interest; and finding the landmarks across a plurality of camera images.

7. The method of claim 5, wherein the tracking phase comprises:

estimating a location of the object of interest based on at least one of object appearance, object motion, or object landmarks; and updating the estimated pose of the object of interest based on the estimated location.

8. The method of claim 1, wherein performing the tracking operation in the first mode comprises:

loading the previously identified biometric data, the previously identified biometric data comprising a hand feature estimate;

computing a three-dimensional model of a hand based on the hand feature estimate; and constraining parameters for tracking of the hand based on the hand feature estimate.

9. The method of claim 8, wherein the hand feature estimate is based on one or more bones of the hand.

10. The method of claim 1, wherein determining, based on the bending data, whether to use the previously identified biometric data in the tracking operation of the XR device comprises:

comparing the bending data to previously stored bending data associated with the previously identified biometric data; and determining that the bending matches the previously stored bending data when the bending data is within an acceptable range of the previously stored bending data.

11. The method of claim 10, wherein the acceptable range is defined by a threshold difference between the bending data and the previously stored bending data.

12. The method of claim 1, wherein determining, based on the bending data, whether to use the previously identified biometric data in the tracking operation of the XR device comprises:

processing the bending data to generate a prediction for biometric data; and comparing the prediction with the previously identified biometric data.

13. The method of claim 1, wherein the selected mode is the first mode, and performing the tracking operation in the first mode comprises:

loading the previously identified biometric data; and initializing the tracking operation using the loaded previously identified biometric data.

14. The method of claim 1, wherein the selected mode is the second mode, and performing the tracking operation in the second mode comprises:

performing a calibration operation to obtain new biometric data;

storing the new biometric data; and performing the tracking operation using the new biometric data.

15. The method of claim 1, wherein the XR device comprises a head-wearable device including a flexible frame configured to bend to accommodate a head of the user.

16. The method of claim 1, wherein obtaining the bending data comprises using one or more strain gauge sensors to detect deformation.

17. The method of claim 1, wherein obtaining the bending data comprises:

measuring a strain of the XR device;

detecting changes in the strain when the XR device bends to accommodate a head of the user wearing the XR device; and generating the bending data based on the changes in the strain.

18. The method of claim 1, wherein the tracking operation comprises tracking hand gestures for user input to the XR device.

19. A system comprising:

at least one processor; and at least one memory storing instructions that, when executed by the at least one processor, configure the system to perform operations comprising:

obtaining bending data indicative of bending of an extended reality (XR) device to accommodate a body part of a user wearing the XR device;

determining, based on the bending data, whether to use previously identified biometric data in a tracking operation of the XR device;

selecting a mode of the XR device, the selected mode being a first mode in which the previously identified biometric data is applied in the tracking operation or a second mode in which previous biometric data is not applied in the tracking operation; and performing, by the XR device, the tracking operation based on the selected mode.

20. One or more non-transitory computer-readable storage media, the computer-readable storage media including instructions that when executed by at least one processor, cause the at least one processor to perform operations comprising:

obtaining bending data indicative of bending of an extended reality (XR) device to accommodate a body part of a user wearing the XR device;

determining, based on the bending data, whether to use previously identified biometric data in a tracking operation of the XR device;

selecting a mode of the XR device, the selected mode being a first mode in which the previously identified biometric data is applied in the tracking operation or a second mode in which previous biometric data is not applied in the tracking operation; and performing, by the XR device, the tracking operation based on the selected mode.

* * * * *